(12) United States Patent
Döller et al.

(10) Patent No.: US 7,504,362 B2
(45) Date of Patent: Mar. 17, 2009

(54) PESTICIDAL COMPOSITIONS

(75) Inventors: Uwe Döller, Rodgau (DE); David Teh-Wei Chou, Bad Soden (DE); Merwyn Steinsberger, Idstein (DE); Michael Maier, Frankfurt (DE); Anke Kuhlmann, Leverkusen (DE); Karl Seeger, Hofheim (DE); David William Hawkins, Upminster Essex (GB); Stanley Thomas Derek Gough, Raleigh, NC (US); David Treadway Manning, Cary, NC (US)

(73) Assignee: Merial Limited, Duluth, GA (US)

( * ) Notice: Subject to any disclaimer, the term of this patent is extended or adjusted under 35 U.S.C. 154(b) by 0 days.

(21) Appl. No.: 10/537,460

(22) PCT Filed: Nov. 12, 2003

(86) PCT No.: PCT/EP03/12618

§ 371 (c)(1),
(2), (4) Date: Jun. 22, 2006

(87) PCT Pub. No.: WO2004/049797

PCT Pub. Date: Jun. 17, 2004

(65) Prior Publication Data

US 2006/0247242 A1 Nov. 2, 2006

(30) Foreign Application Priority Data

Dec. 3, 2002 (EP) .................................. 02027034

(51) Int. Cl.
*A01N 43/56* (2006.01)
*A61K 31/415* (2006.01)
*C07D 231/42* (2006.01)

(52) U.S. Cl. ..................... 504/282; 548/368.1; 514/407
(58) Field of Classification Search .............. 548/368.1; 514/407; 504/282
See application file for complete search history.

(56) References Cited

U.S. PATENT DOCUMENTS

| | | |
|---|---|---|
| 4,631,211 A | 12/1986 | Houghten |
| 4,945,165 A | 7/1990 | Jensen-Korte et al. |
| 5,232,940 A | 8/1993 | Hatton et al. |
| 5,580,843 A | 12/1996 | Stetter et al. |
| 5,939,441 A | 8/1999 | Stetter et al. |
| 6,265,430 B1 | 7/2001 | Alig et al. |

FOREIGN PATENT DOCUMENTS

| | | |
|---|---|---|
| EP | 0 201 852 A2 | 11/1986 |
| EP | 0 234 119 A1 | 9/1987 |
| EP | 0 295 117 B1 | 12/1988 |
| EP | 0 659 745 B1 | 6/1995 |
| EP | 0 679 650 A1 | 11/1995 |
| EP | 0 846 686 B1 | 6/1998 |
| WO | 87/03781 A1 | 7/1987 |
| WO | 93/06089 A1 | 4/1993 |
| WO | 94/21606 A1 | 9/1994 |
| WO | 97/28126 A1 | 8/1997 |
| WO | 98/24769 A1 | 6/1998 |
| WO | 00/35884 A1 | 6/2000 |

OTHER PUBLICATIONS

Sheila H. DeWitt, "Automated Synthesis," Annual Reports in Combinatorial Chemistry and Molecular Diversity, 1997, pp. 69-77, vol. 1, ESCOM Science Publishers B.V.
Richard A. Houghten, "General Method for the Rapid Solid-Phase Synthesis of Large Numbers of Peptides: Specificity of Antigen-Antibody Interaction at the Level of Individual Amino Acids (Simultaneous Multiple-Peptide Synthesis)", Proc. Natl. Acad. Sci. USA, Immunology, Aug. 1985, pp. 5131-5135, vol. 82.

*Primary Examiner*—Patricia L Morris
(74) *Attorney, Agent, or Firm*—Judy Jaracki-Black; Merial Limited; Thomas Kowslski, Esq.

(57) ABSTRACT

5-Substituted-sulfonylaminopyrazole derivatives of formula (I):

$$\text{(I)}$$

or salts thereof, wherein the various symbols are as defined in the description, and pesticidal compositions thereof, processes for their preparation, and methods for their use for the control of arthropods (including insects and arachnids) and helminths (including nematodes).

19 Claims, No Drawings

PESTICIDAL COMPOSITIONS

CROSS-REFERENCE TO RELATED APPLICATIONS

This application is the U.S. national stage of International Appln. No. PCT/EP2003/012618, filed Nov. 12, 2003, which claims priority under 35 U.S.C. §119 of European Patent Application No. 02027034.4, filed Dec. 3, 2002, said applications being expressly incorporated by reference herein in their entireties and relied upon.

The invention relates to 5-substituted-sulfonylaminopyrazole derivatives, processes for their preparation, to compositions thereof, and to their use for the control of pests, such as harmful arthropods (including insects and arachnids) and helminths (including nematodes).

The control of arthropods, such as insects and arachnids, and helminths, such as nematodes with 1-arylpyrazole compounds has been described in, for example, patent publication numbers WO 93/06089, WO 94/21606, WO 87/03781, EP 0295117, EP 659745, EP 679650, EP 201852 and U.S. Pat. No. 5,232,940. The control of parasites in animals with 1-arylpyrazole compounds has also been described in, for example, patent publication numbers WO 00/35884, EP 0846686, WO 98/24769 and WO 97/28126.

However, the level of action and/or duration of action of these prior-art compounds is not entirely satisfactory in all fields of application, in particular against certain organisms or when low concentrations are applied.

Since modern pesticides must meet a wide range of demands, for example regarding level, duration and spectrum of action, use spectrum, toxicity, combination with other active substances, combination with formulation auxiliaries or synthesis, and since the occurrence of resistances is possible, the development of such substances can never be regarded as concluded, and there is constantly a high demand for novel compounds which are advantageous over the known compounds, at least as far as some aspects are concerned.

The present invention provides a compound which is a 5-substituted-sulfonylaminopyrazole derivative of formula (I):

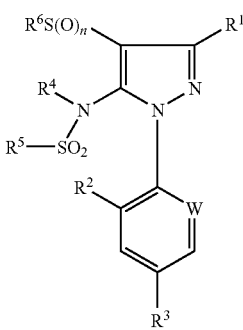

wherein:
$R^1$ is $(C_1-C_6)$-alkyl, $(C_1-C_6)$-haloalkyl, CN, $C(S)NH_2$, or halogen;
W is N, C—$CH_3$ or C-halogen;
$R^2$ is H, $CH_3$ or halogen;
$R^3$ is halo, $(C_1-C_6)$-alkyl, $(C_1-C_6)$-haloalkyl, $(C_1-C_6)$-haloalkoxy, $S(O)_p$—$(C_1-C_6)$-haloalkyl or $SF_5$;
$R^4$ is H, $(C_2-C_6)$-alkenyl, $(C_2-C_6)$-haloalkenyl, $(C_2-C_6)$-alkynyl, $(C_2-C_6)$-haloalkynyl, $(C_3-C_7)$-cycloalkyl, —$CO_2$—$(C_1-C_6)$-alkyl, —$CO_2$—$(C_3-C_7)$-cycloalkyl, —$CO_2$-$(C_1-C_4)$-alkyl-$(C_3-C_7)$-cycloalkyl, —$CO_2$—$(C_3-C_6)$-alkenyl, —$CO_2$—$(C_3-C_6)$-alkynyl, —$CO_2$—$(CH_2)_qR^7$, $CONR^8R^9$, $CO$—$(CH_2)_qR^{11}$, $(CH_2)_qR^7$, $(CH_2)_qR^{10}$, $COR_9$, $COCH_2NR^8R^9$, —CO—$(CH_2)_qR^7$ or —CO—$(CH_2)_qR^{10}$; or $(C_1-C_6)$-alkyl unsubstituted or substituted by one or more radicals selected from the group consisting of halogen, $(C_1-C_6)$-alkoxy, $(C_1-C_6)$-haloalkoxy, $(C_3-C_7)$-cycloalkyl, $S(O)_pR^{11}$, $CO_2$—$(C_1-C_6)$-alkyl, —$O(C=O)$—$(C_1-C_6)$-alkyl, $NR^8R^9$, $CONR^8R^9$, $SO_2NR^8R^9$, OH, CN, $NO_2$, $OR^7$, $OR^{10}$, $NR^8COR^{12}$ and $NR^8SO_2R^{11}$;
$R^5$ is $(C_3-C_7)$-cycloalkyl, $(C_2-C_6)$-alkenyl, $(C_2-C_6)$-haloalkenyl, $R^{13}$, $R^{10}$, $R^{17}$ or —CH=CH—$R^{15}$; or is $(C_1-C_{15})$-alkyl [preferably $(C_1-C_6)$-alkyl] unsubstituted or substituted by one or more radicals selected from the group consisting of halogen, $(C_1-C_6)$-alkoxy, $(C_1-C_6)$-haloalkoxy, $(C_3-C_6)$-alkenyloxy, $(C_3-C_6)$-haloalkenyloxy, $(C_3-C_6)$-alkynyloxy, $(C_3-C_6)$-haloalkynyloxy, $(C_3-C_7)$-cycloalkyl, $S(O)_pR^7$, $S(O)_pR^{10}$, $S(O)_pR^{11}$, CN, $NO_2$, OH, $COR^8$, $NR^8COR^{12}$, $NR^8SO_2R^{11}$, $CONR^8R^9$, $NR^8R^9$, $OR^7$, $OR^{10}$, $R^{13}$, $R^{10}$ and $CO_2R^8$, or a methylene group in the unsubstituted or substituted $(C_1-C_6)$-alkyl is replaced by a group selected from —CO—, —O—, —$S(O)_g$—, —$NR^8$—, —COO—, —OCO—, —$CONR^8$—, —$NR^8CO$—, —C(=$NOR^8$)—, —C(=N—$NR^8R^9$)— and —C(=$NR^8$)— provided that the replacing group is not directly bonded to the $SO_2$ group in formula (I);
$R^6$ and $R^{11}$ are each independently $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl or $(C_3-C_7)$-cycloalkyl;
$R^7$ is phenyl unsubstituted or substituted by one or more radicals selected from the group consisting of halogen, $(C_1-C_6)$-alkyl, $(C_1-C_6)$-haloalkyl, $(C_1-C_6)$-alkoxy, $(C_1-C_6)$-haloalkoxy, CN, $NO_2$, $S(O)_pR^{11}$ and $NR^9R^{12}$;
$R^8$ is H, $(C_1-C_6)$-alkyl, $(C_1-C_6)$-haloalkyl, $(C_3-C_7)$-cycloalkyl, —$(C_1-C_4)$-alkyl-$(C_3-C_7)$-cycloalkyl, —$(CH_2)_qR^7$ or —$(CH_2)_qR^{10}$;
$R^9$ and $R^{12}$ are each independently H, $(C_1-C_6)$-alkyl, $(C_1-C_6)$-haloalkyl, $(C_3-C_7)$-Cycloalkyl or —$(C_1-C_4)$-alkyl-$(C_3-C_7)$-cycloalkyl; or
$R^8$ and $R^9$ together with the attached N atom form a five- or six-membered saturated ring which optionally contains an additional hetero atom in the ring which is selected from O, S and N, the ring being unsubstituted or substituted by one or more radicals selected from the group consisting of halogen, $(C_1-C_6)$-alkyl and $(C_1-C_6)$-haloalkyl;
$R^{10}$ and $R^{20}$ are each independently heterocyclyl unsubstituted or substituted by one or more radicals selected from the group consisting of halogen, $(C_1-C_4)$-alkyl, $(C_1-C_4)$-haloalkyl, $(C_1-C_4)$-alkoxy, $S(O)_pR^{14}$, OH, $OR^7$ and oxo;
$R^{13}$ is aryl unsubstituted or substituted by one or more radicals selected from the group consisting of halogen, $(C_1-C_6)$-alkyl, $(C_1-C_6)$-haloalkyl, $(C_1-C_6)$-alkoxy, $(C_1-C_6)$-haloalkoxy, CN, $NO_2$, $S(O)_pR^{11}$, $SF_5$, $NR^8R^9$, $COR^{11}$, $COR^7$, $CONR^8R^9$, $SO_2NR^8R^9$, OH, $OR^7$, $R^{15}$, $R^6$, $OR^{16}$, $SO_3H$, $(C_1-C_6)$-alkylideneimino, CH=$NOR^{14}$, $S(O)_pR^{18}$, $CO_2R^{19}$ and $R^{20}$;
$R^{14}$ is $(C_1-C_6)$-alkyl or $(C_1-C_6)$-haloalkyl;
$R^{15}$ is phenyl or naphthyl which groups are unsubstituted or substituted by one or more radicals selected from the group consisting of halogen, $(C_1-C_6)$-alkyl, $(C_1-C_6)$-haloalkyl and $(C_1-C_6)$-alkoxy;
$R^{16}$ is a heteroaromatic radical selected from the group consisting of pyridyl, pyrimidinyl, pyridazinyl, pyrazinyl, triazinyl, thienyl, thiazolyl, thiadiazolyl, oxazolyl, isoxazolyl, furyl, pyrrolyl, pyrazolyl, imidazolyl and triazolyl, which groups are unsubstituted or substituted by one or more radicals selected from the group consisting of halogen, $(C_1-C_6)$-alkyl, $(C_1-C_6)$-haloalkyl and $(C_1-C_6)$-alkoxy;

$R^{17}$ is a heteroaromatic radical selected from the group consisting of pyridyl, pyrimidinyl, pyridazinyl, pyrazinyl, triazinyl, thienyl, thiazolyl, thiadiazolyl, oxazolyl, isoxazolyl, furyl, pyrrolyl, pyrazolyl, imidazolyl and triazolyl, which is unsubstituted or substituted by one or more radicals selected from the group consisting of halogen, $(C_1-C_6)$-alkyl, $(C_1-C_6)$-haloalkyl and $(C_1-C_6)$-alkoxy, and which heteroaromatic radical is substituted by $R^{15}$, $R^{16}$ or $OR^{16}$;

$R^{18}$ is phenyl unsubstituted or substituted by one or more radicals selected from the group consisting of halogen, $(C_1-C_6)$-alkyl, $(C_1-C_6)$-haloalkyl and $(C_1-C_6)$-alkoxy;

$R^{19}$ is $(C_1-C_6)$-alkyl, $(C_1-C_6)$-haloalkyl, $R^{18}$ or —$(C_1-C_6)$-alkyl-$(C_1-C_3)$-alkoxy;

n, p and q are each independently zero, one or two; and each heterocyclyl in the above-mentioned radicals is independently a heterocyclic radical having 3 to 6 ring atoms and 1, 2 or 3 hetero atoms in the ring selected from the group consisting of N, O and S;

or a pesticidally acceptable salt thereof.

These compounds possess valuable pesticidal properties.

The invention also encompasses any stereoisomer, enantiomer or geometric isomer, and mixtures thereof.

By the term "pesticidally acceptable salts" is meant salts the anions or cations of which are known and accepted in the art for the formation of salts for pesticidal use. Suitable salts with bases, e.g. formed by compounds of formula (I) containing a carboxylic acid or sulfonamide group, include alkali metal (e.g. sodium and potassium), alkaline earth metal (e.g. calcium and magnesium), ammonium and amine (e.g. diethanolamine, triethanolamine, octylamine, morpholine and dioctylmethylamine) salts. Suitable acid addition salts, e.g. formed by compounds of formula (I) containing an amino group, include salts with inorganic acids, for example hydrochlorides, sulphates, phosphates and nitrates and salts with organic acids for example acetic acid.

In the present patent specification, including the accompanying claims, the aforementioned substituents have the following meanings:

Halogen atom means fluorine, chlorine, bromine or iodine.

The term "halo" before the name of a radical means that this radical is partially or completely halogenated, that is to say, substituted by F, Cl, Br, or I, in any combination, preferably by F or Cl.

Alkyl groups and portions thereof (unless otherwise defined) may be straight- or branched-chain.

The expression "$(C_1-C_6)$-alkyl" is to be understood as meaning an unbranched or branched hydrocarbon radical having 1, 2, 3, 4, 5 or 6 carbon atoms, such as, for example a methyl, ethyl, propyl, isopropyl, 1-butyl, 2-butyl, 2-methylpropyl or tert-butyl radical.

Alkyl radicals and also in composite groups, unless otherwise defined, preferably have 1 to 4 carbon atoms.

"$(C_1-C_6)$Haloalkyl" means an alkyl group mentioned under the expression "$(C_1-C_6)$alkyl" in which one or more hydrogen atoms are replaced by the same number of identical or different halogen atoms, such as monohaloalkyl, perhaloalkyl, $CF_3$, $CHF_2$, $CH_2F$, $CHFCH_3$, $CF_3CH_2$, $CF_3CF_2$, $CHF_2CF_2$, $CH_2FCHCl$, $CH_2Cl$, $CCl_3$, $CHCl_2$ or $CH_2Cl$.

The expression "—$(C_1-C_4)$-alkyl-$(C_3-C_7)$-cycloalkyl" means a $(C_1-C_4)$alkyl group which is substituted by a $(C_3-C_7)$ cycloalkyl ring.

"$(C_1-C_6)$Alkoxy" means an alkoxy group whose carbon chain has the meaning given under the expression "$(C_1-C_6)$ alkyl". "Haloalkoxy" is, for example, $OCF_3$, $OCHF_2$, $OCH_2F$, $CF_3CF_2O$, $OCH_2CF_3$ or $OCH_2CH_2Cl$.

"$(C_2-C_6)$Alkenyl" means an unbranched or branched non-cyclic carbon chain having a number of carbon atoms which corresponds to this stated range and which contains at least one double bond which can be located in any position of the respective unsaturated radical. "$(C_2-C_6)$Alkenyl" accordingly denotes, for example, the vinyl, allyl, 2-methyl-2-propenyl, 2-butenyl, pentenyl, 2-methylpentenyl or the hexenyl group.

"$(C_2-C_6)$Alkynyl" means an unbranched or branched non-cyclic carbon chain having a number of carbon atoms which corresponds to this stated range and which contains one triple bond which can be located in any position of the respective unsaturated radical. "$(C_2-C_6)$Alkynyl" accordingly denotes, for example, the propargyl, 1-methyl-2-propynyl, 2-butynyl or 3-butynyl group.

Cycloalkyl groups preferably have from three to seven carbon atoms in the ring and are optionally substituted by halogen or alkyl.

In compounds of formula (I) the following examples of radicals are provided:

An example of alkyl substituted by cycloalkyl is cyclopropylmethyl;

an example of alkyl substituted by alkoxy is methoxymethyl ($CH_3OCH_2$—); and an example of alkyl substituted by alkylthio is methylthiomethyl ($CH_3SCH_2$—).

Aryl is a mono- or bicyclic aromatic system containing six to 10 ring carbon atoms, for example phenyl, naphthyl, tetrahydronaphthyl, indenyl, indanyl and the like, preferably phenyl.

A "heterocyclyl" group can be saturated, unsaturated or heteroaromatic; it preferably contains one or more, in particular 1, 2 or 3, hetero atoms in the heterocyclic ring, preferably selected from the group consisting of N, O and S; it is preferably an aliphatic heterocyclyl radical having 3 to 7 ring atoms or a heteroaromatic radical having 5 or 6 ring atoms. The heterocyclic radical can be, for example, a heteroaromatic radical or ring (heteroaryl) such as, for example, a mono-, bi- or polycyclic aromatic system in which at least 1 ring contains one or more hetero atoms, for example pyridyl, pyrimidinyl, pyridazinyl, pyrazinyl, triazinyl, thienyl, thiazolyl, thiadiazolyl, oxazolyl, isoxazolyl, furyl, pyrrolyl, pyrazolyl, imidazolyl and triazolyl, or it is a partially or fully hydrogenated radical such as oxiranyl, oxetanyl, oxolanyl (=tetrahydrofuryl), oxanyl, pyrrolidyl, piperidyl, piperazinyl, dioxolanyl, oxazolinyl, isoxazolinyl, oxazolidinyl, isoxazolidinyl and morpholinyl. In addition the term "heterocyclyl" includes fused heterocyclyl groups, for example benzimidazolyl, benzoxazolyl, quinolinyl, phthalimido, indolyl and benzodioxolanyl. The "heterocyclyl" group may be unsubstituted or substituted by one or radicals (preferably 1, 2 or 3 radicals) preferably selected from the group consisting of halogen, alkoxy, haloalkoxy, alkylthio, hydroxyl, amino, nitro, carboxyl, cyano, alkoxycarbonyl, alkylcarbonyl, formyl, carbamoyl, mono- and dialkylaminocarbonyl, substituted amino such as acylamino, mono- and dialkylamino, and alkylsulfinyl, haloalkylsulfinyl, alkylsulfonyl, haloalkylsulfonyl, alkyl and haloalkyl, and additionally also oxo. The oxo group can also be present at those hetero ring atoms where various oxidation numbers are possible, for example in the case of N and S.

The term pests means arthropod pests (including insects and arachnids), and helminths (including nematodes).

Preferably $R^1$ is CN.

Preferably W is C—Cl.

Preferably $R^2$ is chlorine.

Preferably $R^3$ is $CF_3$ or $OCF_3$ (more preferably $R^3$ is $CF_3$).

Preferably $R^4$ is H, $(C_3-C_6)$-alkenyl, $(C_3-C_6)$-alkynyl, $(C_3-C_7)$-cycloalkyl, —$CO_2$-$(C_1-C_6)$-alkyl, —$(CH_2)_qR^7$ or $COCH_2NR^8R^9$; or $(C_1-C_6)$-alkyl unsubstituted or substituted by one or more radicals selected from the group consisting of halogen, $(C_3-C_7)$-cycloalkyl and $S(O)_pR^{11}$. More preferably $R^4$ is methyl.

Preferably $R^5$ is $R^{13}$ or $R^{10}$; or $(C_1-C_6)$-alkyl unsubstituted or substituted by one or more radicals selected from the group consisting of halogen, $R^{13}$ and $R^{10}$.

Preferably $R^6$ is $(C_1-C_2)$-haloalkyl (more preferably $R^6$ is $CF_3$).

Preferably $R^7$ is phenyl unsubstituted or substituted by one or more radicals selected from the group consisting of halogen, $(C_1-C_3)$-alkyl, $(C_1-C_3)$-haloalkyl, $(C_1-C_3)$-alkoxy, $(C_1-C_3)$-haloalkoxy, $S(O)_pR^{11}$ and $NR^9R^{12}$ (more preferably $R^7$ is phenyl unsubstituted or substituted by one or more radicals selected from the group consisting of halogen, $(C_1-C_2)$-alkyl, $(C_1-C_2)$-haloalkyl and $(C_1-C_2)$-alkoxy).

Preferably $R^8$ is H, $(C_1-C_6)$-alkyl or $(C_1-C_6)$-haloalkyl (more preferably $R^8$ is H or $(C_1-C_3)$-alkyl).

Preferably $R^9$ and $R^{12}$ are each independently H, $(C_1-C_3)$-alkyl or $(C_1-C_3)$-haloalkyl; or $R^8$ and $R^9$ together with the attached N atom form a five- or six-membered saturated ring which optionally contains an additional hetero atom in the ring which is selected from O, S and N, the ring being unsubstituted or substituted by one or more radicals selected from the group consisting of halogen and $(C_1-C_3)$-alkyl (more preferably $R^9$ is H or $(C_1-C_3)$-alkyl).

Preferably $R^{10}$ is heterocyclyl unsubstituted or substituted by one or more radicals selected from the group consisting of halogen, $(C_1-C_3)$-alkyl, $(C_1-C_3)$-haloalkyl, $(C_1-C_3)$-alkoxy, $S(O)_pR^4$, OH and oxo (more preferably $R^{10}$ is heterocyclyl unsubstituted or substituted by one or more radicals selected from the group consisting of halogen, $(C_1-C_2)$-alkyl, $(C_1-C_2)$-haloalkyl, $(C_1-C_2)$-alkoxy and $S(O)_pR^{14}$).

Preferably $R^{11}$ and $R^{14}$ are each independently $(C_1-C_3)$-alkyl or $(C_1-C_3)$-haloalkyl.

Preferably $R^{13}$ is phenyl unsubstituted or substituted by one or more radicals selected from the group consisting of halogen, $(C_1-C_6)$-alkyl, $(C_1-C_6)$-haloalkyl, $(C_1-C_6)$-alkoxy, $(C_1-C_6)$-haloalkoxy, CN, $NO_2$, $S(O)_pR^{11}$, $NR^8R^9$, $COR^{11}$, $COR^7$, $CONR^8R^9$, $SO_2NR^8R^9$, OH, $SO_3H$ and $(C_1-C_6)$-alkylideneimino (more preferably $R^{13}$ is phenyl unsubstituted or substituted by one or more radicals selected from the group consisting of halogen, $(C_1-C_2)$-alkyl, $(C_1-C_2)$-haloalkyl, $(C_1-C_2)$-alkoxy, $(C_1-C_2)$-haloalkoxy, CN, $NO_2$, $S(O)_pR^{11}$ and $NR^8R^9$).

Preferably q is 0 or 1.

Preferably each heterocyclyl in the above-mentioned radicals is independently a heteroaromatic radical having 5 or 6 ring atoms and 1, 2 or 3 hetero atoms in the ring selected from the group consisting of N, O and S (more preferably each heterocyclyl in the above-mentioned radicals is independently a heteroaromatic radical selected from the group consisting of pyridyl, pyrimidinyl, pyridazinyl, pyrazinyl, triazinyl, thienyl, thiazolyl, thiadiazolyl, oxazolyl, isoxazolyl, furyl, pyrrolyl, pyrazolyl, imidazolyl and triazolyl).

A preferred class of compounds of formula (I) are those in which:

$R^1$ is $(C_1-C_6)$-alkyl, $(C_1-C_6)$-haloalkyl, CN, $C(S)NH_2$, or halogen;

W is N, C—$CH_3$ or C-halogen;

$R^2$ is H, $CH_3$ or halogen;

$R^3$ is halo, $(C_1-C_6)$-alkyl, $(C_1-C_6)$-haloalkyl, $(C_1-C_6)$-haloalkoxy, $S(O)_p$—$(C_1-C_6)$-haloalkyl or $SF_5$;

$R^4$ is H, $(C_2-C_6)$-alkenyl, $(C_2-C_6)$-haloalkenyl, $(C_2-C_6)$-alkynyl, $(C_2-C_6)$-haloalkynyl, $(C_3-C_7)$-cycloalkyl, —$CO_2$—$(C_1-C_6)$-alkyl, —$CO_2$—$(C_3-C_7)$-cycloalkyl, —$CO_2$—$(C_1-C_4)$-alkyl-$(C_3-C_7)$-cycloalkyl, —$CO_2$—$(C_3-C_6)$-alkenyl, —$CO_2$—$(C_3-C_6)$-alkynyl, —$CO_2$—$(CH_2)_qR^7$, $CONR^8R^9$, —$CO_2$—$(CH_2)_qR^{10}$, —$(CH_2)_qR^7$, $(CH_2)_qR^{10}$, $COR^9$, $COCH_2NR^8R^9$, —CO—$(CH_2)_qR^7$ or —CO—$(CH_2)_qR^{10}$; or $(C_1-C_6)$-alkyl unsubstituted or substituted by one or more radicals selected from the group consisting of halogen, $(C_1-C_6)$-alkoxy, $(C_1-C_6)$-haloalkoxy, $(C_3-C_7)$-cycloalkyl, $S(O)_pR^{11}$, $CO_2$—$(C_1-C_6)$-alkyl, —O(C=O)—$(C_1-C_6)$-alkyl, $NR^8R^9$, $CONR^8R^9$, $SO_2NR^8R^9$, OH, CN, $NO_2$, $OR^7$, $OR^{10}$, $NR^8COR^{12}$ and $NR^8SO_2R^{11}$;

$R^5$ is $(C_3-C_7)$-Cycloalkyl, $(C_2-C_6)$-alkenyl, $(C_2-C_6)$-haloalkenyl, $R^{13}$, $R^{10}$, $R^{17}$ or —CH=CH—$R^{15}$; or is $(C_1-C_6)$-alkyl unsubstituted or substituted by one or more radicals selected from the group consisting of halogen, $(C_1-C_6)$-alkoxy, $(C_1-C_6)$-haloalkoxy, $(C_3-C_6)$-alkenyloxy, $(C_3-C_6)$-haloalkenyloxy, $(C_3-C_6)$-alkynyloxy, $(C_3-C_6)$-haloalkynyloxy, $(C_3-C_7)$-cycloalkyl, $S(O)_pR^7$, $S(O)_pR^{10}$, $S(O)_pR^{11}$, CN, $NO_2$, OH, $COR^8$, $NR^8COR^{12}$, $NR^8SO_2R^{11}$, $CONR^8R^9$, $NR^8R^9$, $OR^7$, $OR^{10}$, $R^{13}$, $R^{10}$ and $CO_2R^8$, or a methylene group in the unsubstituted or substituted $(C_1-C_6)$-alkyl is replaced by a group selected from —CO—, —O—, —$S(O)_p$—, —$NR^8$—, —COO—, —OCO—, —$CONR^8$—, —$NR^8CO$—, —C(=$NOR^8$)—, —C(=N—$NR^8R^9$)— and —C(=$NR^8$)— provided that the replacing group is not directly bonded to the $SO_2$ group in formula (I);

$R^6$ and $R^{11}$ are each independently $(C_1-C_6)$-alkyl, $(C_1-C_6)$-haloalkyl, $(C_2-C_6)$-alkenyl $(C_2-C_6)$-haloalkenyl, $(C_2-C_6)$-alkynyl, $(C_2-C_6)$-haloalkynyl or $(C_3-C_7)$-cycloalkyl;

$R^7$ is phenyl unsubstituted or substituted by one or more radicals selected from the group consisting of halogen, $(C_1-C_6)$-alkyl, $(C_1-C_6)$-haloalkyl, $(C_1-C_6)$-alkoxy, $(C_1-C_6)$-haloalkoxy, CN, $NO_2$, $S(O)_pR^{11}$ and $NR^9R^{12}$;

$R^8$ is H, $(C_1-C_6)$-alkyl, $(C_1-C_6)$-haloalkyl, $(C_3-C_7)$-cycloalkyl, —$(C_1-C_4)$-alkyl-$(C_3-C_7)$-cycloalkyl, —$(CH_2)_qR^7$ or —$(CH_2)_qR^{10}$;

$R^9$ and $R^{12}$ are each independently H, $(C_1-C_6)$-alkyl, $(C_1-C_6)$-haloalkyl, $(C_3-C_7)$-cycloalkyl or —$(C_1-C_4)$-alkyl-$(C_3-C_7)$-cycloalkyl; or $R^8$ and $R^9$ together with the attached N atom form a five- or six-membered saturated ring which optionally contains an additional hetero atom in the ring which is selected from O, S and N, the ring being unsubstituted or substituted by one or more radicals selected from the group consisting of halogen, $(C_1-C_6)$-alkyl and $(C_1-C_6)$-haloalkyl;

$R^{10}$ is heterocyclyl unsubstituted or substituted by one or more radicals selected from the group consisting of halogen, $(C_1-C_4)$-alkyl, $(C_1-C_4)$-haloalkyl, $(C_1-C_4)$-alkoxy, $S(O)_pR^{14}$, OH, $OR^7$ and oxo;

$R^{13}$ is aryl unsubstituted or substituted by one or more radicals selected from the group consisting of halogen, $(C_1-C_6)$-alkyl, $(C_1-C_6)$-haloalkyl, $(C_1-C_6)$-alkoxy, $(C_1-C_6)$-haloalkoxy, CN, $NO_2$, $S(O)_pR^{11}$, $SF_5$, $NR^8R^9$, $COR^{11}$, $COR^7$, $CONR^8R^9$, $SO_2NR^8R^9$, OH, $OR^7$, $R^{15}$, $R^{16}$, $OR^{16}$, $SO_3H$ and $(C_1-C_6)$-alkylideneimino;

$R^{14}$ is $(C_1-C_6)$-alkyl or $(C_1-C_6)$-haloalkyl;

$R^{15}$ is phenyl or naphthyl which groups are unsubstituted or substituted by one or more radicals selected from the group consisting of halogen, $(C_1-C_6)$-alkyl, $(C_1-C_6)$-haloalkyl and $(C_1-C_6)$-alkoxy;

$R^{16}$ is a heteroaromatic radical selected from the group consisting of pyridyl, pyrimidinyl, pyridazinyl, pyrazinyl, triazinyl, thienyl, thiazolyl, thiadiazolyl, oxazolyl, isoxazolyl, furyl, pyrrolyl, pyrazolyl, imidazolyl and triazolyl, which groups are unsubstituted or substituted by one or more radicals selected from the group consisting of halogen, $(C_1-C_6)$-alkyl, $(C_1-C_6)$-haloalkyl and $(C_1-C_6)$-alkoxy;

$R^{17}$ is a heteroaromatic radical selected from the group consisting of pyridyl, pyrimidinyl, pyridazinyl, pyrazinyl, triazinyl, thienyl, thiazolyl, thiadiazolyl, oxazolyl, isoxazolyl, furyl, pyrrolyl, pyrazolyl, imidazolyl and triazolyl, which is unsubstituted or substituted by one or more radicals selected from the group consisting of halogen, $(C_1-C_6)$-alkyl, $(C_1-C_6)$-haloalkyl and $(C_1-C_6)$-alkoxy, and which heteroaromatic radical is substituted by $R^{15}$, $R^{16}$ or $OR^{16}$;

n, p and q are each independently zero, one or two; and each heterocyclyl in the above-mentioned radicals is independently a heterocyclic radical having 3 to 6 ring atoms and 1, 2 or 3 hetero atoms in the ring selected from the group consisting of N, O and S.

A further preferred class of compounds of formula (I) are those in which:

$R^1$ is CN;

W is C—Cl;

$R^2$ is chlorine;

$R^3$ is $CF_3$ or $OCF_3$;

$R^4$ is H, $(C_3-C_6)$-alkenyl, $(C_3-C_6)$-alkynyl, $(C_3-C_7)$-cycloalkyl, $—CO_2—(C_1-C_6)$-alkyl, $—(CH_2)_qR^7$ or $COCH_2NR^8R^9$; or $(C_1-C_6)$-alkyl unsubstituted or substituted by one or more radicals selected from the group consisting of halogen, $(C_3-C_7)$-cycloalkyl and $S(O)_pR^{11}$ (more preferably $R^4$ is methyl);

$R^5$ is $R^{13}$ or $R^{10}$; or $(C_1-C_6)$-alkyl unsubstituted or substituted by one or more radicals selected from the group consisting of halogen, $R^{13}$ and $R^{10}$;

$R^6$ is $(C_1-C_2)$-haloalkyl;

$R^7$ is phenyl unsubstituted or substituted by one or more radicals selected from the group consisting of halogen, $(C_1-C_3)$-alkyl, $(C_1-C_3)$-haloalkyl, $(C_1-C_3)$-alkoxy, $(C_1-C_3)$-haloalkoxy, $S(O)_pR^{11}$ and $NR^9R^{12}$;

$R^8$ is H, $(C_1-C_6)$-alkyl or $(C_1-C_6)$-haloalkyl;

$R^9$ and $R^{12}$ are each independently H, $(C_1-C_3)$-alkyl or $(C_1-C_3)$-haloalkyl; or $R^8$ and $R^9$ together with the attached N atom form a five- or six-membered saturated ring which optionally contains an additional hetero atom in the ring which is selected from O, S and N, the ring being unsubstituted or substituted by one or more radicals selected from the group consisting of halogen and $(C_1-C_3)$-alkyl;

$R^{10}$ is heterocyclyl unsubstituted or substituted by one or more radicals selected from the group consisting of halogen, $(C_1-C_3)$-alkyl, $(C_1-C_3)$-haloalkyl, $(C_1-C_3)$-alkoxy, $S(O)_pR^{14}$, OH and oxo;

$R^{11}$ and $R^{14}$ are each independently $(C_1-C_3)$-alkyl or $(C_1-C_3)$-haloalkyl;

$R^{13}$ is phenyl unsubstituted or substituted by one or more radicals selected from the group consisting of halogen, $(C_1-C_6)$-alkyl, $(C_1-C_6)$-haloalkyl, $(C_1-C_6)$-alkoxy, $(C_1-C_6)$-haloalkoxy, CN, $NO_2$, $S(O)_pR^{11}$, $NR^8R^9$, $COR^{11}$, $COR^7$, $CONR^8R^9$, $SO_2NR^8R^9$, OH, $SO_3H$ and $(C_1-C_6)$-alkylideneimino;

n, p and q are each independently 0, 1 or 2; and each heterocyclyl in the above-mentioned radicals is independently a heteroaromatic radical having 5 or 6 ring atoms and 1, 2 or 3 hetero atoms in the ring selected from the group consisting of N, O and S.

A more preferred class of compounds of formula (I) are those in which:

$R^1$ is CN;

W is C—Cl;

$R^2$ is chlorine;

$R^3$ is $CF_3$;

$R^4$ is H, $(C_3-C_4)$-alkenyl, $(C_3-C_4)$-alkynyl, $(C_3-C_6)$-cycloalkyl, $—CO_2—(C_1-C_3)$-alkyl, $—(CH_2)_qR^7$ or $COCH_2NR^8R^9$; or $(C_1-C_4)$-alkyl unsubstituted or substituted by one or more radicals selected from the group consisting of halogen, $(C_3-C_6)$-cycloalkyl and $S(O)_pR^{11}$ (more preferably $R^4$ is methyl);

$R^5$ is $R^{13}$ or $R^{10}$; or $(C_1-C_4)$-alkyl unsubstituted or substituted by one or more radicals selected from the group consisting of halogen, $R^{13}$ and $R^{10}$;

$R^6$ is $CF_3$;

$R^7$ is phenyl unsubstituted or substituted by one or more radicals selected from the group consisting of halogen, $(C_1-C_2)$-alkyl, $(C_1-C_2)$-haloalkyl and $(C_1-C_2)$-alkoxy;

$R^8$ is H or $(C_1-C_3)$-alkyl;

$R^9$ is H or $(C_1-C_3)$-alkyl;

$R^{10}$ is heterocyclyl unsubstituted or substituted by one or more radicals selected from the group consisting of halogen, $(C_1-C_2)$-alkyl, $(C_1-C_2)$-haloalkyl, $(C_1-C_2)$-alkoxy and $S(O)_pR^{14}$;

$R^{11}$ and $R^{14}$ are each independently $(C_1-C_2)$-alkyl or $(C_1-C_2)$-haloalkyl;

$R^{13}$ is phenyl unsubstituted or substituted by one or more radicals selected from the group consisting of halogen, $(C_1-C_2)$-alkyl, $(C_1-C_2)$-haloalkyl, $(C_1-C_2)$-alkoxy, $(C_1-C_2)$-haloalkoxy, CN, $NO_2$, $S(O)_pR^{11}$ and $NR^8R^9$;

n and p are each independently 0, 1 or 2;

q is 0 or 1; and each heterocyclyl in the above-mentioned radicals is independently a heteroaromatic radical selected from the group consisting of pyridyl, pyrimidinyl, pyridazinyl, pyrazinyl, triazinyl, thienyl, thiazolyl, thiadiazolyl, oxazolyl, isoxazolyl, furyl, pyrrolyl, pyrazolyl, imidazolyl and triazolyl.

A further preferred class of compounds of formula (I) are those in which:

$R^1$ is CN;

W is C—Cl;

$R^2$ is chlorine;

$R^3$ is $CF_3$;

$R^4$ is H, $(C_3-C_4)$-alkenyl, $(C_3-C_4)$-alkynyl, $(C_3-C_6)$-cycloalkyl, $—CO_2—(C_1-C_3)$-alkyl or $—(CH_2)_qR^7$ in which $R^7$ is phenyl unsubstituted or substituted by one or more halogen radicals; or $(C_1-C_4)$-alkyl unsubstituted or substituted by one or more radicals selected from the group consisting of halogen, $(C_3-C_6)$-cycloalkyl and $S(O)_pR^{11}$ in which $R^{11}$ is $(C_1-C_4)$-alkyl or $(C_1-C_4)$-haloalkyl (more preferably $R^4$ is methyl);

$R^5$ is $(C_3-C_6)$-cycloalkyl; or is phenyl, benzyl or phenethyl which last three mentioned groups are unsubstituted or substituted by one or more radicals selected from the group consisting of halogen, $(C_1-C_4)$-alkyl or $(C_1-C_4)$-haloalkyl, ($C_1$-$C_4$)-alkoxy, ($C_1$-$C_4$)-haloalkoxy, phenyl, naphthyl, —$CO_2$—($C_1$-$C_4$)-alkyl, phenoxy unsubstituted or substituted by one or more halogen radicals, and $S(O)_pR^{11}$ in which $R^{11}$ is ($C_1$-$C_4$)-alkyl or ($C_1$-$C_4$)-haloalkyl; or is $R^{10}$ or —$CH_2R^{10}$ in which $R^{10}$ is pyridyl; pyrimidyl, thienyl, pyrazolyl, imidazoloyl, thiazolyl, pyrrolyl, tetrazolyl, triazolyl or furyl unsubstituted or substituted by one or more halogen radicals; or is ($C_1$-$C_4$)-alkyl unsubstituted or substituted by one or more radicals selected from the group consisting of halogen, $S(O)_pR^{11}$ in which $R^{11}$ is ($C_1$-$C_4$)-alkyl or ($C_1$-$C_4$)-haloalkyl and $NR^8R^9$; in which $R^8$ and $R^9$ are each independently H or ($C_1$-$C_4$)-alkyl;

$R^6$ is $CF_3$;

n and p are each independently 0, 1 or 2; and q is 0 or 1.

A further preferred class of compounds of formula (I) are those in which:

$R^1$ is CN;

W is C—Cl;

$R^2$ is chlorine;

$R^3$ is $CF_3$;

$R^4$ is H, ($C_3$-$C_4$)-alkenyl, ($C_3$-$C_4$)-alkynyl, ($C_3$-$C_6$)-cycloalkyl, —$CO_2$—($C_1$-$C_3$)-alkyl or —$(CH_2)_qR^7$ in which $R^7$ is phenyl unsubstituted or substituted by one or more halogen radicals; or ($C_1$-$C_4$)-alkyl unsubstituted or substituted by one or more radicals selected from the group consisting of halogen, ($C_1$-$C_4$)-alkoxy and ($C_3$-$C_6$)-cycloalkyl (more preferably $R^4$ is methyl);

$R^5$ is ($C_3$-$C_4$)-alkenyl, ($C_3$-$C_6$)-cycloalkyl or CH═CH-phenyl; or ($C_1$-$C_4$)-alkyl unsubstituted or substituted by one or more radicals selected from the group consisting of halogen, $S(O)_p(C_1$-$C_4)$-alkyl, ($C_1$-$C_4$)-alkoxy and $NR^8R^9$ in which $R^8$ and $R^9$ are each independently H or ($C_1$-$C_4$)-alkyl, or together with the attached N atom form a five- or six-membered saturated ring which optionally contains an additional hetero atom in the ring which is selected from O, S and N;

$R^6$ is $CF_3$;

n and p are each independently 0, 1 or 2; and q is 0 or 1.

A further preferred class of compounds of formula (I) are those in which:

$R^1$ is CN;

W is C—Cl;

$R^2$ is chlorine;

$R^3$ is $CF_3$;

$R^4$ is ($C_1$-$C_4$)-alkyl (more preferably $R^4$ is methyl);

$R^5$ is phenyl unsubstituted or substituted by one or more radicals selected from the group consisting of halogen, ($C_1$-$C_4$)-alkyl, ($C_1$-$C_4$)-haloalkyl, ($C_3$-$C_6$)-cycloalkyl, ($C_1$-$C_4$)-alkoxy, ($C_1$-$C_4$)-haloalkoxy, $S(O)_p(C_1$-$C_4)$-alkyl, $S(O)_p(C_1$-$C_4)$-haloalkyl, $NO_2$, $SF_5$, naphthyl, —$CO_2$—($C_1$-$C_4$)-alkyl and benzodioxofanyl; or phenyl substituted by phenoxy which last mentioned group is unsubstituted or substituted by one or more radicals selected from the group consisting of halogen, ($C_1$-$C_4$)-alkyl, ($C_1$-$C_4$)-haloalkyl and ($C_1$-$C_4$)-alkoxy; or phenyl substituted by phenyl which last mentioned group is unsubstituted or substituted by one or more radicals selected from the group consisting of halogen, ($C_1$-$C_4$)-alkyl, ($C_1$-$C_4$)-haloalkyl and ($C_1$-$C_4$)-alkoxy;

$R^6$ is $CF_3$; and n and p are each independently 0, 1 or 2.

A further preferred class of compounds of formula (I) are those in which:

$R^1$ is CN;

W is C—Cl;

$R^2$ is chlorine;

$R^3$ is $CF_3$;

$R^4$ is ($C_1$-$C_4$)-alkyl (more preferably $R^4$ is methyl);

$R^5$ is pyridyl, pyrimidyl, pyrazolyl, imidazoloyl, thiazolyl, pyrrolyl, tetrazolyl, triazolyl, furyl, tetrahydrofuryl or tetrahydrothienyl, which last 11 mentioned groups are unsubstituted or substituted by one or more radicals selected from the group consisting of halogen, ($C_1$-$C_4$)-alkyl and ($C_1$-$C_4$)-haloalkyl; or thienyl unsubstituted or substituted by one or more radicals selected from the group consisting of halogen, ($C_1$-$C_4$)-alkyl, ($C_1$-$C_4$)-haloalkyl and pyridyl;

$R^6$ is $CF_3$; and n is 0, 1 or 2.

The compounds of general formula (I) can be prepared by the application or adaptation of known methods (i.e. methods heretofore used or described in the chemical literature.

In the following description of processes when symbols appearing in formulae are not specifically defined, it is understood that they are "as defined above" in accordance with the first definition of each symbol in the specification.

According to a further feature of the invention compounds of formula (I) wherein $R^1$, $R^2$, $R^3$, $R^4$, $R^5$, $R^6$, W and n are as defined above may be prepared by the reaction of a compound of formula (II):

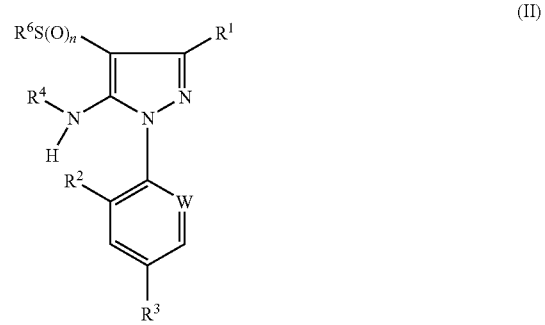

(II)

wherein $R^1$, $R^2$, $R^3$, $R^4$, $R^6$, W and n are as defined above, with a compound of formula (III):

$R^5$—$SO_2L^1$ (III)

wherein $R^5$ is as defined above and $L^1$ is a leaving group, generally halogen and preferably chlorine. The reaction is generally performed in the presence of a base such as sodium hydride, in a solvent such as dioxan, tetrahydrofuran or N,N-dimethylformamide, at a temperature of from 0° to 100° C. (preferably 0° to 50° C.).

According to a further feature of the invention compounds of formula (I) wherein $R^1$, $R^2$, $R^3$, $R^5$, $R^6$, W and n are as defined above and $R^4$ is as defined above with the exclusion of hydrogen, may also be prepared by the alkylation or acylation of the corresponding compound of formula (I) wherein $R^4$ is hydrogen. The alkylation or acylation reactions may be carried out according to the general methods described in patent publication numbers WO 93/06089, WO 94/21606, WO 87/03781, EP 0295117 and U.S. Pat. No. 5,232,940.

According to a further feature of the invention compounds of formula (I) wherein $R^1$, $R^2$, $R^3$, $R^4$, $R^5$, $R^6$ and W are as defined above, and n is 1 or 2 may be prepared by oxidising a corresponding compound in which n is 0 or 1. The oxidation is generally performed using a peracid such as 3-chloroperbenzoic acid in a solvent such as dichloromethane or 1,2-dichloroethane, at a temperature of from 0° C. to the reflux temperature of the solvent.

Collections of compounds of the formula (I) which can be synthesized by the above mentioned process may also be prepared in a parallel manner, and this may be effected manually or in a semiautomated or fully automated manner. In this case, it is possible, for example, to automate the procedure of the reaction, work-up or purification of the products or of the intermediates. In total, this is to be understood as meaning a procedure as is described, for example, by S. H. DeWitt in "Annual Reports in Combinatorial Chemistry and Molecular Diversity: Automated Synthesis", Volume 1, Verlag Escom 1997, pages 69 to 77.

A series of commercially available apparatuses as are offered by, for example, Stem Corporation, Woodrolfe Road, Tollesbury, Essex, CM9 8SE, England or H+ P Labortechnik GmbH, Bruckmannring 28, 85764 Oberschleißheim, Germany or Radleys, Shirehill, Saffron Walden, Essex, England, may be used for the parallel procedure of the reaction and work-up. For the parallel purification of compounds of the formula (I), or of intermediates obtained during the preparation, use may be made, inter alia, of chromatography apparatuses, for example those by ISCO, Inc., 4700 Superior Street, Lincoln, Nebr. 68504, USA.

The apparatuses mentioned lead to a modular procedure in which the individual process steps are automated, but manual operations must be performed between the process steps. This can be prevented by employing semi-integrated or fully integrated automation systems where the automation modules in question are operated by, for example, robots. Such automation systems can be obtained, for example, from Zymark Corporation, Zymark Center, Hopkinton, Mass. 01748, USA.

In addition to what has been described here, compounds of the formula (I) may be prepared in part or fully by solid-phase-supported methods. For this purpose, individual intermediate steps or all intermediate steps of the synthesis or of a synthesis adapted to suit the procedure in question are bound to a synthetic resin. Solid-phase-supported synthesis methods are described extensively in the specialist literature, for example Barry A. Bunin in "The Combinatorial Index", Academic Press, 1998.

The use of solid-phase-supported synthesis methods permits a series of protocols which are known from the literature and which, in turn, can be performed manually or in an automated manner. For example, the "tea-bag method" (Houghten, U.S. Pat. No. 4,631,211; Houghten et al., Proc. Natl. Acad. Sci, 1985, 82, 5131-5135), in which products by IRORI, 11149 North Torrey Pines Road, La Jolla, Calif. 92037, USA, are employed, may be semiautomated. The automation of solid-phase-supported parallel syntheses is performed successfully, for example, by apparatuses by Argonaut Technologies, Inc., 887 Industrial Road, San Carlos, Calif. 94070, USA or MultiSynTech GmbH, Wullener Feld 4, 58454 Witten, Germany.

The preparation of the processes described herein yields compounds of the formula (I) in the form of substance collections which are termed libraries. The present invention also relates to libraries which comprise at least two compounds of the formula (I).

Intermediates of formula (II) wherein L is chlorine, bromine or iodine may be prepared according to known procedures, for example as described in EP 0295117, by the diazotisation of the corresponding amine of formula (VIII), generally using an alkyl nitrite such as t-butyl nitrite, in the presence of a suitable halogenating agent, preferably bromoform, iodine or anhydrous cupric chloride, optionally in the presence of a solvent such as acetonitrile or chloroform, at a temperature of from 0° to 100° C.

Compounds of formula (II) and (III) are known or may be prepared by known methods.

The following non-limiting Examples illustrate the preparation of the compounds of formula (I).

CHEMICAL EXAMPLES

Example 1

1-(2,6-Dichloro-4-trifluoromethylphenyl)-3-cyano-5-(N-benzylsulfonyl-N-methylamino)-4-trifluoromethylsulfinylpyrazole (Compound Number 2-16)

To a solution of 1-(2,6-dichloro-4-trifluoromethylphenyl)-3-cyano-5-methylamino-4-trifluoromethylsulfinylpyrazole (2.0 g, 4.0 mmol) in tetrahydrofuran was added sodium hydride (60%, 0.144 g, 6.0 mmol). After stirring for 1 hour at 20° C. benzylsulfonyl chloride (1.14 g, 6.0 mmol) was added dropwise. The mixture was stirred for an additional 8 hours at 20° C. Aqueous ammonium chloride was added and extractive workup with aqueous sodium carbonate and dichloromethane gave a solid which was washed with heptane-ethyl acetate (1:1), filtered and dried to give the title product (1.5 g, Compound 2-16) as a pale white solid, m.p. 161° C.

Example 2

1-(2,6-Dichloro-4-trifluoromethylphenyl)-5-[N-(3-chloropropylsulfonyl)-N-methylamino]-3-cyano-4-trifluoromethylsulfonylpyrazole (Compound Number 1-121)

To a solution of 1-(2,6-dichloro-4-trifluoromethylphenyl)-3-cyano-5-methylamino-4-trifluoromethylsulfonylpyrazole (1.0 g, 2.1 mmol) in tetrahydrofuran was added sodium hydride (60%, 0.1 g, 3.0 mmol). After stirring for 1 hour at 20° C., 3-chorpropylsulfonyl chloride (0.52 g, 3.0 mmol) was added dropwise. The mixture was stirred for an additional 8 hours at 20° C. Aqueous ammonium chloride was added and extractive workup with aqueous sodium carbonate and dichloromethane gave a solid which was washed with heptane-ethyl acetate (1:1), filtered and dried to give the title product (0.15 g, Compound 1-121) as a pale brown solid.

Example 3

1-(2,6-Dichloro-4-trifluoromethylphenyl)-5-[N-(4-chlorophenylsulfonyl)-N-methylamino]-3-cyano-4-trifluoromethylthiopyrazole (Compound Number 5-3)

To a solution of 1-(2,6-dichloro-4-trifluoromethylphenyl)-3-cyano-5-methylamino-4-trifluoromethylthiopyrazole (0.5 g, 1.0 mmol) in tetrahydrofuran was added 4-dimethylaminopyridine (0.12 g, 1.0 mmol) and triethylamine (0.4 g, 4.0 mmol). After stirring for 30 minutes at 20° C., 4-chorphenylsulfonyl chloride (0.63 g, 3.0 mmol) was added dropwise, and the mixture was heated at reflux for 10 hours. After extractive workup with aqueous sodium carbonate and dichloromethane the product was purified by chromatography eluting with heptane-dichloromethane (1:1) to give the title product (0.02 g, Compound 5-3) as a solid.

The following preferred compounds shown in Tables 1 to 7 also form part of the present invention, and were or may be prepared in accordance with, or analogously to, the above-mentioned Examples 1 to 3 or the above-described general methods. In the Tables, i-Pr means isopropyl, t-Bu means tert-butyl, Ph means phenyl and 4-(3,5-Cl2-PhO) means 4-(3,5-dichlorophenoxy)-. Where subscripts are omitted after atoms it will be understood that they are intended, for example CH₃ means $CH_3$. Double and triple bonds are not explicitly shown. The carbon atom on the left side of the $R^4$ values is bonded to the N atom depicted in formula (I), and the carbon atom on the left side of the $R^5$ values is bonded to the $SO_2$ group depicted in formula (I). Compound numbers are given for reference purposes only.

TABLE 1

Compounds of formula (I) in which $R^1$ is CN; $R^2$ is Cl; W is C—Cl; $R^3$ is $CF_3$ and $R^6$ is $CF_3$.

| Compound Number | $R^4$ | $R^5$ | n | m. p. (° C.)/1H NMR NCH3 |
|---|---|---|---|---|
| 1-1 | H | CH3 | 0 | |
| 1-2 | CH3 | CH3 | 0 | 152 |
| 1-3 | CH2CH3 | CH3 | 0 | |
| 1-4 | CH2CH2CH3 | CH3 | 0 | |
| 1-5 | CH2CH2CH2CH3 | CH3 | 0 | |
| 1-6 | CH2CHCH2 | CH3 | 0 | |
| 1-7 | CH2CCH | CH3 | 0 | |
| 1-8 | C(O)OCH3 | CH3 | 0 | |
| 1-9 | C(O)OCH2CH3 | CH3 | 0 | |
| 1-10 | CH2OCH3 | CH3 | 0 | |
| 1-11 | CH2OCH2CH3 | CH3 | 0 | |
| 1-12 | CH2cyclopropyl | CH3 | 0 | |
| 1-13 | cyclopropyl | CH3 | 0 | |
| 1-14 | CH2Ph | CH3 | 0 | |
| 1-15 | H | CH3 | 1 | |
| 1-16 | CH3 | CH3 | 1 | 164 |
| 1-17 | CH2CH3 | CH3 | 1 | |
| 1-18 | CH2CH2CH3 | CH3 | 1 | |
| 1-19 | CH2CH2CH2CH3 | CH3 | 1 | |
| 1-20 | CH2CHCH2 | CH3 | 1 | |
| 1-21 | CH2CCH | CH3 | 1 | |
| 1-22 | C(O)OCH3 | CH3 | 1 | |
| 1-23 | C(O)OCH2CH3 | CH3 | 1 | |
| 1-24 | CH2OCH3 | CH3 | 1 | |
| 1-25 | CH2OCH2CH3 | CH3 | 1 | |
| 1-26 | CH2cyclopropyl | CH3 | 1 | |
| 1-27 | cyclopropyl | CH3 | 1 | |
| 1-28 | CH2Ph | CH3 | 1 | |
| 1-29 | H | CH3 | 2 | |
| 1-30 | CH3 | CH3 | 2 | |
| 1-31 | CH2CH3 | CH3 | 2 | |
| 1-32 | CH2CH2CH3 | CH3 | 2 | |
| 1-33 | CH2CH2CH2CH3 | CH3 | 2 | |
| 1-34 | CH2CHCH2 | CH3 | 2 | |
| 1-35 | CH2CCH | CH3 | 2 | |
| 1-36 | C(O)OCH3 | CH3 | 2 | |
| 1-37 | C(O)OCH2CH3 | CH3 | 2 | |
| 1-38 | CH2OCH3 | CH3 | 2 | |
| 1-39 | CH2OCH2CH3 | CH3 | 2 | |
| 1-40 | CH2cyclopropyl | CH3 | 2 | |
| 1-41 | cyclopropyl | CH3 | 2 | |
| 1-42 | CH2Ph | CH3 | 2 | |
| 1-43 | H | CH2CH3 | 0 | |
| 1-44 | CH3 | CH2CH3 | 0 | 114 |
| 1-45 | CH2CH3 | CH2CH3 | 0 | |
| 1-46 | CH2CH2CH3 | CH2CH3 | 0 | |
| 1-47 | CH2CH2CH2CH3 | CH2CH3 | 0 | |
| 1-48 | CH2CHCH2 | CH2CH3 | 0 | |
| 1-49 | CH2CCH | CH2CH3 | 0 | |
| 1-50 | C(O)OCH3 | CH2CH3 | 0 | |
| 1-51 | C(O)OCH2CH3 | CH2CH3 | 0 | |
| 1-52 | CH2OCH3 | CH2CH3 | 0 | |
| 1-53 | CH2OCH2CH3 | CH2CH3 | 0 | |
| 1-54 | CH2cyclopropyl | CH2CH3 | 0 | |
| 1-55 | cyclopropyl | CH2CH3 | 0 | |
| 1-56 | CH2Ph | CH2CH3 | 0 | |
| 1-57 | H | CH2CH3 | 1 | oil |
| 1-58 | CH3 | CH2CH3 | 1 | 131 |
| 1-59 | CH2CH3 | CH2CH3 | 1 | |
| 1-60 | CH2CH2CH3 | CH2CH3 | 1 | |
| 1-61 | CH2CH2CH2CH3 | CH2CH3 | 1 | |
| 1-62 | CH2CHCH2 | CH2CH3 | 1 | |
| 1-63 | CH2CCH | CH2CH3 | 1 | |
| 1-64 | C(O)OCH3 | CH2CH3 | 1 | |
| 1-65 | C(O)OCH2CH3 | CH2CH3 | 1 | |
| 1-66 | CH2OCH3 | CH2CH3 | 1 | |
| 1-67 | CH2OCH2CH3 | CH2CH3 | 1 | |
| 1-68 | CH2cyclopropyl | CH2CH3 | 1 | |
| 1-69 | cyclopropyl | CH2CH3 | 1 | |
| 1-70 | CH2Ph | CH2CH3 | 1 | |
| 1-71 | H | CH2CH3 | 2 | |
| 1-72 | CH3 | CH2CH3 | 2 | |
| 1-73 | CH2CH3 | CH2CH3 | 2 | |
| 1-74 | CH2CH2CH3 | CH2CH3 | 2 | |
| 1-75 | CH2CH2CH2CH3 | CH2CH3 | 2 | |
| 1-76 | CH2CHCH2 | CH2CH3 | 2 | |
| 1-77 | CH2CCH | CH2CH3 | 2 | |
| 1-78 | C(O)OCH3 | CH2CH3 | 2 | |
| 1-79 | C(O)OCH2CH3 | CH2CH3 | 2 | |
| 1-80 | CH2OCH3 | CH2CH3 | 2 | |
| 1-81 | CH2OCH2CH3 | CH2CH3 | 2 | |
| 1-82 | CH2cyclopropyl | CH2CH3 | 2 | |
| 1-83 | cyclopropyl | CH2CH3 | 2 | |
| 1-84 | CH2Ph | CH2CH3 | 2 | |
| 1-85 | CH3 | iPr | 1 | 3.38s, 3H |
| 1-86 | CH3 | CH2CH2CH3 | 1 | 140 |
| 1-87 | CH3 | CH2CH2CH2CH3 | 1 | 3.38s, 3H |
| 1-88 | CH3 | CHCl2 | 1 | |
| 1-89 | CH3 | CH2Cl | 1 | 112 |
| 1-90 | CH3 | CF3 | 1 | 112 |
| 1-91 | CH3 | CFH2 | 1 | |
| 1-92 | CH3 | CF2H | 1 | |
| 1-93 | CH3 | C8H17 | 1 | |
| 1-94 | CH3 | C9H19 | 1 | |
| 1-95 | CH3 | C10H21 | 1 | |
| 1-96 | CH3 | C12H25 | 1 | |
| 1-97 | CH3 | CHCH2 | 1 | 143 |
| 1-98 | CH3 | CH2CHCH2 | 1 | |
| 1-99 | CH3 | cyclo-C5H9 | 1 | |
| 1-100 | CH3 | cyclo-C6H11 | 1 | |
| 1-101 | CH3 | CH2CH2CH2Cl | 1 | 3.40s, 3H |
| 1-102 | CH3 | CH2SO2CH3 | 1 | |
| 1-103 | CH3 | CH2NH2 | 1 | |
| 1-104 | CH3 | CH2NHCH3 | 1 | |
| 1-105 | CH3 | CH2N(CH3)2 | 1 | |
| 1-106 | CH3 | CH2NHCH2CH3 | 1 | |
| 1-107 | CH3 | CH2N(CH2CH3)2 | 1 | |
| 1-108 | CH3 | CH2CH2N(CH3)2 | 1 | |
| 1-109 | CH3 | CH2CH2N(CH2CH3)2 | 1 | |
| 1-110 | CH3 | CH2-N-morpholinyl | 1 | |
| 1-111 | CH3 | CH2OCH3 | 1 | |
| 1-112 | CH3 | CH2OCH2CH3 | 1 | |
| 1-113 | CH3 | CH2SCH3 | 1 | |
| 1-114 | CH3 | CHCHPh | 1 | 123 |
| 1-115 | CH3 | CHCHPh | 2 | 138 |
| 1-116 | Na | CH3 | 0 | |
| 1-117 | H | CH2CH3 | 1 | |
| 1-118 | CH3 | CCl3 | 1 | 99 |
| 1-119 | CH3 | CHCl2 | 1 | 3.58s, 3H |
| 1-120 | CH3 | CH2CH2CH2CH3 | 2 | |
| 1-121 | CH3 | CH2CH2CH2Cl | 2 | 102 |
| 1-122 | CH3 | iPr | 0 | 3.40s, 3H |
| 1-123 | CH3 | C8H17 | 1 | |
| 1-124 | CH3 | C9H19 | 0 | 3.36s, 3H |
| 1-125 | CH3 | C10H21 | 0 | 3.38s, 3H |
| 1-126 | CH3 | C12H25 | 1 | 91 |
| 1-127 | CH3 | C8H17 | 2 | 3.42s, 3H |

TABLE 1-continued

Compounds of formula (I) in which R¹ is CN; R² is Cl; W is C—Cl; R³ is CF₃ and R⁶ is CF₃.

| Compound Number | R⁴ | R⁵ | n | m.p. (°C.)/1H NMR NCH3 |
|---|---|---|---|---|
| 1-128 | CH3 | C8H17 | 0 | 3.36s, 3H |
| 1-129 | CH3 | C12H25 | 0 | 3.38s, 3H |

TABLE 2

Compounds of formula (Ia)

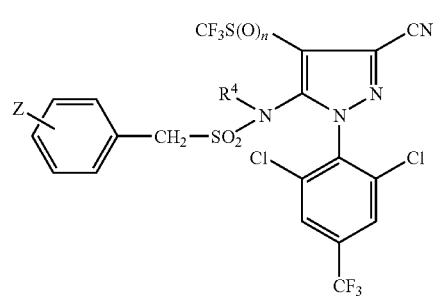

| Compound Number | R⁴ | Z | n | m.p. (°C.) |
|---|---|---|---|---|
| 2-1 | H | H | 0 | |
| 2-2 | CH3 | H | 0 | |
| 2-3 | CH2CH3 | H | 0 | |
| 2-4 | CH2CH2CH3 | H | 0 | |
| 2-5 | CH2CH2CH2CH3 | H | 0 | |
| 2-6 | CH2CHCH2 | H | 0 | |
| 2-7 | CH2CCH | H | 0 | |
| 2-8 | C(O)OCH3 | H | 0 | |
| 2-9 | C(O)OCH2CH3 | H | 0 | |
| 2-10 | CH2OCH3 | H | 0 | |
| 2-11 | CH2OCH2CH3 | H | 0 | |
| 2-12 | CH2cyclopropyl | H | 0 | |
| 2-13 | cyclopropyl | H | 0 | |
| 2-14 | CH2Ph | H | 0 | |
| 2-15 | H | H | 1 | |
| 2-16 | CH3 | H | 1 | 161 |
| 2-17 | CH2CH3 | H | 1 | |
| 2-18 | CH2CH2CH3 | H | 1 | |
| 2-19 | CH2CH2CH2CH3 | H | 1 | |
| 2-20 | CH2CHCH2 | H | 1 | |
| 2-21 | CH2CCH | H | 1 | |
| 2-22 | C(O)OCH3 | H | 1 | |
| 2-23 | C(O)OCH2CH3 | H | 1 | |
| 2-24 | CH2OCH3 | H | 1 | |
| 2-25 | CH2OCH2CH3 | H | 1 | |
| 2-26 | CH2cyclopropyl | H | 1 | |
| 2-27 | cyclopropyl | H | 1 | |
| 2-28 | CH2Ph | H | 1 | |
| 2-29 | H | H | 2 | |
| 2-30 | CH3 | H | 2 | |
| 2-31 | CH2CH3 | H | 2 | |
| 2-32 | CH2CH2CH3 | H | 2 | |
| 2-33 | CH2CH2CH2CH3 | H | 2 | |
| 2-34 | CH2CHCH2 | H | 2 | |
| 2-35 | CH2CCH | H | 2 | |
| 2-36 | C(O)OCH3 | H | 2 | |
| 2-37 | C(O)OCH2CH3 | H | 2 | |
| 2-38 | CH2OCH3 | H | 2 | |
| 2-39 | CH2OCH2CH3 | H | 2 | |
| 2-40 | CH2cyclopropyl | H | 2 | |
| 2-41 | cyclopropyl | H | 2 | |
| 2-42 | CH2Ph | H | 2 | |

TABLE 2-continued

Compounds of formula (Ia)

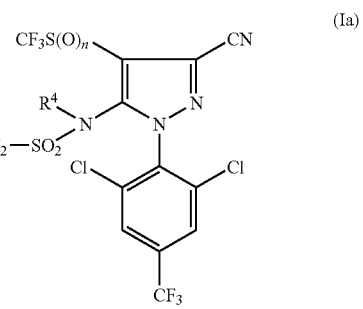

| Compound Number | R⁴ | Z | n | m.p. (°C.) |
|---|---|---|---|---|
| 2-43 | CH3 | 2-Cl | 0 | |
| 2-44 | CH3 | 3-Cl | 0 | |
| 2-45 | CH3 | 4-Cl | 0 | |
| 2-46 | CH3 | 2,5-Cl2 | 0 | |
| 2-47 | CH3 | 2,6-Cl2 | 0 | |
| 2-48 | CH3 | 3,4-Cl2 | 0 | |
| 2-49 | CH3 | 2-F | 0 | |
| 2-50 | CH3 | 3-F | 0 | |
| 2-51 | CH3 | 4-F | 0 | |
| 2-52 | CH3 | 3,4-F2 | 0 | |
| 2-53 | CH3 | 2,6-F2 | 0 | |
| 2-54 | CH3 | 4-Br | 0 | |
| 2-55 | CH3 | 4-I | 0 | |
| 2-56 | CH3 | 2-CF3 | 0 | |
| 2-57 | CH3 | 3-CF3 | 0 | |
| 2-58 | CH3 | 4-CF3 | 0 | |
| 2-59 | CH3 | 3,5-(CF3)2 | 0 | |
| 2-60 | CH3 | 4-CF3, 2-Cl | 0 | |
| 2-61 | CH3 | 3-CF3, 4-Cl | 0 | |
| 2-62 | CH3 | 2-OCH3 | 0 | |
| 2-63 | CH3 | 3-OCH3 | 0 | |
| 2-64 | CH3 | 4-OCH3 | 0 | |
| 2-65 | CH3 | 4-SCH3 | 0 | |
| 2-66 | CH3 | 4-SCF3 | 0 | |
| 2-67 | CH3 | 4-SF5 | 0 | |
| 2-68 | CH3 | 3,4-(OCH3)2 | 0 | |
| 2-69 | CH3 | 4-Ph | 0 | |
| 2-70 | CH3 | 4-I | 0 | |
| 2-71 | CH3 | 2-CH3 | 0 | |
| 2-72 | CH3 | 3-CH3 | 0 | |
| 2-73 | CH3 | 2,3-(CH3)2 | 0 | |
| 2-74 | CH3 | 4-CH3 | 0 | |
| 2-75 | CH3 | 2,5-(CH3)2 | 0 | |
| 2-76 | CH3 | 2,6-(CH3)2 | 0 | |
| 2-77 | CH3 | 3,4-(CH3)2 | 0 | |
| 2-78 | CH3 | 2-Cl | 1 | |
| 2-79 | CH3 | 3-Cl | 1 | 199 |
| 2-80 | CH3 | 4-Cl | 1 | |
| 2-81 | CH3 | 2,5-Cl2 | 1 | |
| 2-82 | CH3 | 2,6-Cl2 | 1 | |
| 2-83 | CH3 | 3,4-Cl2 | 1 | 223 |
| 2-84 | CH3 | 2-F | 1 | |
| 2-85 | CH3 | 3-F | 1 | |
| 2-86 | CH3 | 4-F | 1 | 207 |
| 2-87 | CH3 | 3,4-F2 | 1 | |
| 2-88 | CH3 | 2,6-F2 | 1 | |
| 2-89 | CH3 | 4-Br | 1 | |
| 2-90 | CH3 | 4-I | 1 | |
| 2-91 | CH3 | 2-CF3 | 1 | |
| 2-92 | CH3 | 3-CF3 | 1 | |
| 2-93 | CH3 | 4-CF3 | 1 | |
| 2-94 | CH3 | 3,5-(CF3)2 | 1 | |
| 2-95 | CH3 | 4-CF3, 2-Cl | 1 | |
| 2-96 | CH3 | 3-CF3, 4-Cl | 1 | |
| 2-97 | CH3 | 2-OCH3 | 1 | |
| 2-98 | CH3 | 3-OCH3 | 1 | |
| 2-99 | CH3 | 4-OCH3 | 1 | |

TABLE 2-continued

Compounds of formula (Ia)

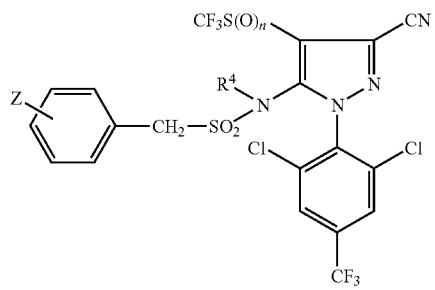

| Compound Number | R⁴ | Z | n | m.p. (° C.) |
|---|---|---|---|---|
| 2-100 | CH3 | 4-SCH3 | 1 | |
| 2-101 | CH3 | 4-SCF3 | 1 | |
| 2-102 | CH3 | 4-SF5 | 1 | |
| 2-103 | CH3 | 3,4-(OCH3)2 | 1 | |
| 2-104 | CH3 | 4-Ph | 1 | |
| 2-105 | CH3 | 4-I | 1 | |
| 2-106 | CH3 | 2-CH3 | 1 | |
| 2-107 | CH3 | 3-CH3 | 1 | |
| 2-108 | CH3 | 2,3-(CH3)2 | 1 | |
| 2-109 | CH3 | 4-CH3 | 1 | |
| 2-110 | CH3 | 2,5-(CH3)2 | 1 | |
| 2-111 | CH3 | 2,6-(CH3)2 | 1 | |
| 2-112 | CH3 | 3,4-(CH3)2 | 1 | |
| 2-113 | CH3 | 2-Cl | 2 | |
| 2-114 | CH3 | 3-Cl | 2 | |
| 2-115 | CH3 | 4-Cl | 2 | |
| 2-116 | CH3 | 2,5-Cl2 | 2 | |
| 2-117 | CH3 | 2,6-Cl2 | 2 | |
| 2-118 | CH3 | 3,4-Cl2 | 2 | |
| 2-119 | CH3 | 2-F | 2 | |
| 2-120 | CH3 | 3-F | 2 | |
| 2-121 | CH3 | 4-F | 2 | |
| 2-122 | CH3 | 3,4-F2 | 2 | |
| 2-123 | CH3 | 2,6-F2 | 2 | |
| 2-124 | CH3 | 4-Br | 2 | |
| 2-125 | CH3 | 4-I | 2 | |
| 2-126 | CH3 | 2-CF3 | 2 | |

TABLE 2-continued

Compounds of formula (Ia)

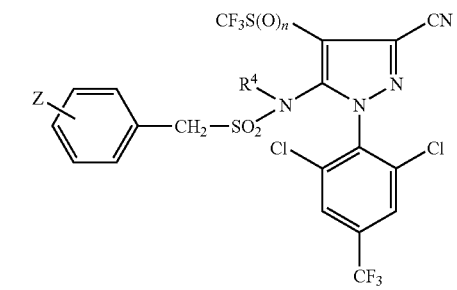

| Compound Number | R⁴ | Z | n | m.p. (° C.) |
|---|---|---|---|---|
| 2-127 | CH3 | 3-CF3 | 2 | |
| 2-128 | CH3 | 4-CF3 | 2 | |
| 2-129 | CH3 | 3,5-(CF3)2 | 2 | |
| 2-130 | CH3 | 4-CF3, 2-Cl | 2 | |
| 2-131 | CH3 | 3-CF3, 4-Cl | 2 | |
| 2-132 | CH3 | 2-OCH3 | 2 | |
| 2-133 | CH3 | 3-OCH3 | 2 | |
| 2-134 | CH3 | 4-OCH3 | 2 | |
| 2-135 | CH3 | 4-SCH3 | 2 | |
| 2-136 | CH3 | 4-SCF3 | 2 | |
| 2-137 | CH3 | 4-SF5 | 2 | |
| 2-138 | CH3 | 3,4-(OCH3)2 | 2 | |
| 2-139 | CH3 | 4-Ph | 2 | |
| 2-140 | CH3 | 4-I | 2 | |
| 2-141 | CH3 | 2-CH3 | 2 | |
| 2-142 | CH3 | 3-CH3 | 2 | |
| 2-143 | CH3 | 2,3-(CH3)2 | 2 | |
| 2-144 | CH3 | 4-CH3 | 2 | |
| 2-145 | CH3 | 2,5-(CH3)2 | 2 | |
| 2-146 | CH3 | 2,6-(CH3)2 | 2 | |
| 2-147 | CH3 | 3,4-(CH3)2 | 2 | |
| 2-148 | CH3 | 4-C5H11 | 0 | |
| 2-149 | CH3 | 3,5-Cl2 | 0 | |
| 2-150 | CH3 | 3,5-Cl2 | 1 | |
| 2-151 | CH3 | 3,5-Cl2 | 2 | |

TABLE 3

Compounds of formula (Ib)

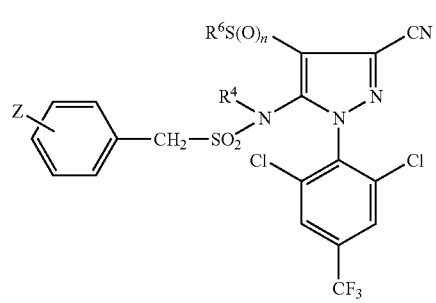

| Compound Number | R⁶ | R⁴ | Z | n | m.p. (° C.) |
|---|---|---|---|---|---|
| 3-1 | CFCl2 | H | H | 0 | |
| 3-2 | CFCl2 | CH3 | H | 0 | |
| 3-3 | CFCl2 | CH2CH3 | H | 0 | |

TABLE 3-continued

Compounds of formula (Ib)

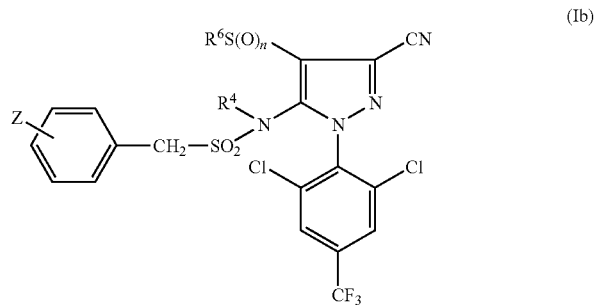

| Compound Number | $R^6$ | $R^4$ | Z | n | m.p. (° C.) |
|---|---|---|---|---|---|
| 3-4 | CFCl2 | CH2CH2CH3 | H | 0 | |
| 3-5 | CFCl2 | CH2CH2CH2CH3 | H | 0 | |
| 3-6 | CFCl2 | CH2CHCH2 | H | 0 | |
| 3-7 | CFCl2 | CH2CCH | H | 0 | |
| 3-8 | CFCl2 | C(O)OCH3 | H | 0 | |
| 3-9 | CFCl2 | C(O)OCH2CH3 | H | 0 | |
| 3-10 | CFCl2 | CH2OCH3 | H | 0 | |
| 3-11 | CFCl2 | CH2OCH2CH3 | H | 0 | |
| 3-12 | CFCl2 | CH2cyclopropyl | H | 0 | |
| 3-13 | CFCl2 | cyclopropyl | H | 0 | |
| 3-14 | CFCl2 | CH2Ph | H | 0 | |
| 3-15 | CFCl2 | H | H | 1 | |
| 3-16 | CFCl2 | CH3 | H | 1 | wax |
| 3-17 | CFCl2 | CH2CH3 | H | 1 | |
| 3-18 | CFCl2 | CH2CH2CH3 | H | 1 | |
| 3-19 | CFCl2 | CH2CH2CH2CH3 | H | 1 | |
| 3-20 | CFCl2 | CH2CHCH2 | H | 1 | |
| 3-21 | CFCl2 | CH2CCH | H | 1 | |
| 3-22 | CFCl2 | C(O)OCH3 | H | 1 | |
| 3-23 | CFCl2 | C(O)OCH2CH3 | H | 1 | |
| 3-24 | CFCl2 | CH2OCH3 | H | 1 | |
| 3-25 | CFCl2 | CH2OCH2CH3 | H | 1 | |
| 3-26 | CFCl2 | CH2cyclopropyl | H | 1 | |
| 3-27 | CFCl2 | cyclopropyl | H | 1 | |
| 3-28 | CFCl2 | CH2Ph | H | 1 | |
| 3-39 | CFCl2 | H | H | 2 | |
| 3-30 | CFCl2 | CH3 | H | 2 | |
| 3-31 | CFCl2 | CH2CH3 | H | 2 | |
| 3-32 | CFCl2 | CH2CH2CH3 | H | 2 | |
| 3-33 | CFCl2 | CH2CH2CH2CH3 | H | 2 | |
| 3-34 | CFCl2 | CH2CHCH2 | H | 2 | |
| 3-35 | CFCl2 | CH2CCH | H | 2 | |
| 3-36 | CFCl2 | C(O)OCH3 | H | 2 | |
| 3-37 | CFCl2 | C(O)OCH2CH3 | H | 2 | |
| 3-38 | CFCl2 | CH2OCH3 | H | 2 | |
| 3-39 | CFCl2 | CH2OCH2CH3 | H | 2 | |
| 3-40 | CFCl2 | CH2cyclopropyl | H | 2 | |
| 3-41 | CFCl2 | cyclopropyl | H | 2 | |
| 3-42 | CFCl2 | CH2Ph | H | 2 | |
| 3-43 | CFCl2 | CH3 | 2-Cl | 0 | |
| 3-44 | CFCl2 | CH3 | 3-Cl | 0 | |
| 3-45 | CFCl2 | CH3 | 4-Cl | 0 | |
| 3-46 | CFCl2 | CH3 | 2,5-Cl2 | 0 | |
| 3-47 | CFCl2 | CH3 | 2,6-Cl2 | 0 | |
| 3-48 | CFCl2 | CH3 | 3,4-Cl2 | 0 | |
| 3-49 | CFCl2 | CH3 | 2-F | 0 | |
| 3-50 | CFCl2 | CH3 | 3-F | 0 | |
| 3-51 | CFCl2 | CH3 | 4-F | 0 | |
| 3-52 | CFCl2 | CH3 | 3,4-F2 | 0 | |
| 3-53 | CFCl2 | CH3 | 2,6-F2 | 0 | |
| 3-54 | CFCl2 | CH3 | 4-Br | 0 | |
| 3-55 | CFCl2 | CH3 | 4-I | 0 | |
| 3-56 | CFCl2 | CH3 | 2-CF3 | 0 | |
| 3-57 | CFCl2 | CH3 | 3-CF3 | 0 | |
| 3-58 | CFCl2 | CH3 | 4-CF3 | 0 | |
| 3-59 | CFCl2 | CH3 | 3,5-(CF3)2 | 0 | |
| 3-60 | CFCl2 | CH3 | 4-CF3, 2-Cl | 0 | |

TABLE 3-continued

Compounds of formula (Ib)

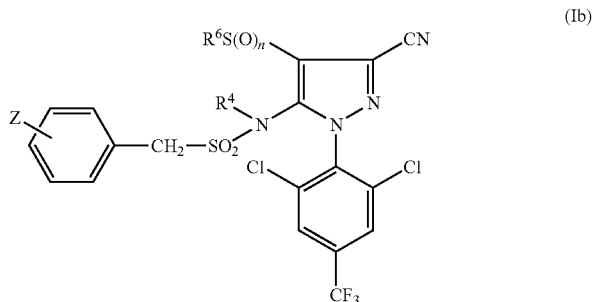

| Compound Number | R$^6$ | R$^4$ | Z | n | m.p. (° C.) |
|---|---|---|---|---|---|
| 3-61 | CFCl2 | CH3 | 3-CF3, 4-Cl | 0 | |
| 3-62 | CFCl2 | CH3 | 2-OCH3 | 0 | |
| 3-63 | CFCl2 | CH3 | 3-OCH3 | 0 | |
| 3-64 | CFCl2 | CH3 | 4-OCH3 | 0 | |
| 3-65 | CFCl2 | CH3 | 4-SCH3 | 0 | |
| 3-66 | CFCl2 | CH3 | 4-SCF3 | 0 | |
| 3-67 | CFCl2 | CH3 | 4-SF5 | 0 | |
| 3-68 | CFCl2 | CH3 | 3,4-(OCH3)2 | 0 | |
| 3-69 | CFCl2 | CH3 | 4-Ph | 0 | |
| 3-70 | CFCl2 | CH3 | 4-I | 0 | |
| 3-71 | CFCl2 | CH3 | 2-CH3 | 0 | |
| 3-72 | CFCl2 | CH3 | 3-CH3 | 0 | |
| 3-73 | CFCl2 | CH3 | 2,3-(CH3)2 | 0 | |
| 3-74 | CFCl2 | CH3 | 4-CH3 | 0 | |
| 3-75 | CFCl2 | CH3 | 2,5-(CH3)2 | 0 | |
| 3-76 | CFCl2 | CH3 | 2,6-(CH3)2 | 0 | |
| 3-77 | CFCl2 | CH3 | 3,4-(CH3)2 | 0 | |
| 3-78 | CFCl2 | CH3 | 2-Cl | 1 | |
| 3-79 | CFCl2 | CH3 | 3-Cl | 1 | |
| 3-80 | CFCl2 | CH3 | 4-Cl | 1 | |
| 3-81 | CFCl2 | CH3 | 2,5-Cl2 | 1 | |
| 3-82 | CFCl2 | CH3 | 2,6-Cl2 | 1 | |
| 3-83 | CFCl2 | CH3 | 3,4-Cl2 | 1 | |
| 3-84 | CFCl2 | CH3 | 2-F | 1 | |
| 3-85 | CFCl2 | CH3 | 3-F | 1 | |
| 3-86 | CFCl2 | CH3 | 4-F | 1 | |
| 3-87 | CFCl2 | CH3 | 3,4-F2 | 1 | |
| 3-88 | CFCl2 | CH3 | 2,6-F2 | 1 | |
| 3-89 | CFCl2 | CH3 | 4-Br | 1 | |
| 3-90 | CFCl2 | CH3 | 4-I | 1 | |
| 3-91 | CFCl2 | CH3 | 2-CF3 | 1 | |
| 3-92 | CFCl2 | CH3 | 3-CF3 | 1 | |
| 3-93 | CFCl2 | CH3 | 4-CF3 | 1 | |
| 3-94 | CFCl2 | CH3 | 3,5-(CF3)2 | 1 | |
| 3-95 | CFCl2 | CH3 | 4-CF3, 2-Cl | 1 | |
| 3-96 | CFCl2 | CH3 | 3-CF3, 4-Cl | 1 | |
| 3-97 | CFCl2 | CH3 | 2-OCH3 | 1 | |
| 3-98 | CFCl2 | CH3 | 3-OCH3 | 1 | |
| 3-99 | CFCl2 | CH3 | 4-OCH3 | 1 | |
| 3-100 | CFCl2 | CH3 | 4-SCH3 | 1 | |
| 3-101 | CFCl2 | CH3 | 4-SCF3 | 1 | |
| 3-102 | CFCl2 | CH3 | 4-SF5 | 1 | |
| 3-103 | CFCl2 | CH3 | 3,4-(OCH3)2 | 1 | |
| 3-104 | CFCl2 | CH3 | 4-Ph | 1 | |
| 3-105 | CFCl2 | CH3 | 4-I | 1 | |
| 3-106 | CFCl2 | CH3 | 2-CH3 | 1 | |
| 3-107 | CFCl2 | CH3 | 3-CH3 | 1 | |
| 3-108 | CFCl2 | CH3 | 2,3-(CH3)2 | 1 | |
| 3-109 | CFCl2 | CH3 | 4-CH3 | 1 | |
| 3-110 | CFCl2 | CH3 | 2,5-(CH3)2 | 1 | |
| 3-111 | CFCl2 | CH3 | 2,6-(CH3)2 | 1 | |
| 3-112 | CFCl2 | CH3 | 3,4-(CH3)2 | 1 | |
| 3-113 | CFCl2 | CH3 | 2-Cl | 2 | |
| 3-114 | CFCl2 | CH3 | 3-Cl | 2 | |
| 3-115 | CFCl2 | CH3 | 4-Cl | 2 | |
| 3-116 | CFCl2 | CH3 | 2,5-Cl2 | 2 | |
| 3-117 | CFCl2 | CH3 | 2,6-Cl2 | 2 | |

TABLE 3-continued

Compounds of formula (Ib)

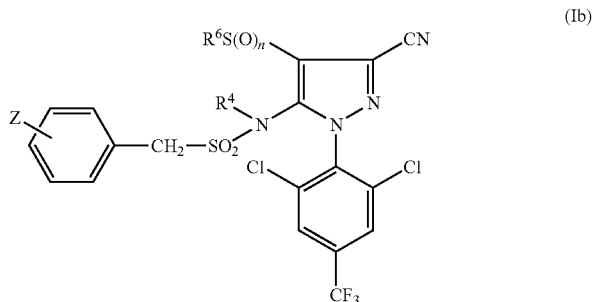

| Compound Number | $R^6$ | $R^4$ | Z | n | m.p. (° C.) |
|---|---|---|---|---|---|
| 3-118 | CFCl2 | CH3 | 3,4-Cl2 | 2 | |
| 3-119 | CFCl2 | CH3 | 2-F | 2 | |
| 3-120 | CFCl2 | CH3 | 3-F | 2 | |
| 3-121 | CFCl2 | CH3 | 4-F | 2 | |
| 3-122 | CFCl2 | CH3 | 3,4-F2 | 2 | |
| 3-123 | CFCl2 | CH3 | 2,6-F2 | 2 | |
| 3-124 | CFCl2 | CH3 | 4-Br | 2 | |
| 3-125 | CFCl2 | CH3 | 4-I | 2 | |
| 3-126 | CFCl2 | CH3 | 2-CF3 | 2 | |
| 3-127 | CFCl2 | CH3 | 3-CF3 | 2 | |
| 3-128 | CFCl2 | CH3 | 4-CF3 | 2 | |
| 3-129 | CFCl2 | CH3 | 3,5-(CF3)2 | 2 | |
| 3-130 | CFCl2 | CH3 | 4-CF3, 2-Cl | 2 | |
| 3-131 | CFCl2 | CH3 | 3-CF3, 4-Cl | 2 | |
| 3-132 | CFCl2 | CH3 | 2-OCH3 | 2 | |
| 3-133 | CFCl2 | CH3 | 3-OCH3 | 2 | |
| 3-134 | CFCl2 | CH3 | 4-OCH3 | 2 | |
| 3-135 | CFCl2 | CH3 | 4-SCH3 | 2 | |
| 3-136 | CFCl2 | CH3 | 4-SCF3 | 2 | |
| 3-137 | CFCl2 | CH3 | 4-SF5 | 2 | |
| 3-138 | CFCl2 | CH3 | 3,4-(OCH3)2 | 2 | |
| 3-139 | CFCl2 | CH3 | 4-Ph | 2 | |
| 3-140 | CFCl2 | CH3 | 4-I | 2 | |
| 3-141 | CFCl2 | CH3 | 2-CH3 | 2 | |
| 3-142 | CFCl2 | CH3 | 3-CH3 | 2 | |
| 3-143 | CFCl2 | CH3 | 2,3-(CH3)2 | 2 | |
| 3-144 | CFCl2 | CH3 | 4-CH3 | 2 | |
| 3-145 | CFCl2 | CH3 | 2,5-(CH3)2 | 2 | |
| 3-146 | CFCl2 | CH3 | 2,6-(CH3)2 | 2 | |
| 3-147 | CFCl2 | CH3 | 3,4-(CH3)2 | 2 | |
| 3-148 | CF2Cl | CH3 | H | 0 | |
| 3-149 | CF2H | CH3 | H | 0 | |
| 3-150 | CFH2 | CH3 | H | 0 | |
| 3-151 | CH3 | CH3 | H | 0 | |
| 3-152 | CH2CH3 | CH3 | H | 0 | |
| 3-153 | CCl2CF3 | CH3 | H | 0 | |
| 3-154 | CH2CF3 | CH3 | H | 2 | |
| 3-155 | CHClCF3 | CH3 | H | 0 | |
| 3-156 | CFHCF2H | CH3 | H | 0 | |
| 3-157 | CFHCFH2 | CH3 | H | 0 | |
| 3-148 | CF2Cl | CH3 | H | 1 | |
| 3-149 | CF2H | CH3 | H | 1 | |
| 3-150 | CFH2 | CH3 | H | 1 | |
| 3-151 | CH3 | CH3 | H | 1 | |
| 3-152 | CH2CH3 | CH3 | H | 1 | |
| 3-153 | CCl2CF3 | CH3 | H | 1 | |
| 3-154 | CH2CF3 | CH3 | H | 1 | |
| 3-155 | CHClCF3 | CH3 | H | 1 | |
| 3-156 | CFHCF2H | CH3 | H | 1 | |
| 3-157 | CFHCFH2 | CH3 | H | 1 | |
| 3-148 | CF2Cl | CH3 | H | 2 | |
| 3-149 | CF2H | CH3 | H | 2 | |
| 3-150 | CFH2 | CH3 | H | 2 | |
| 3-151 | CH3 | CH3 | H | 2 | |
| 3-152 | CH2CH3 | CH3 | H | 2 | |
| 3-153 | CCl2CF3 | CH3 | H | 2 | |
| 3-154 | CH2CF3 | CH3 | H | 2 | |

TABLE 3-continued

Compounds of formula (Ib)

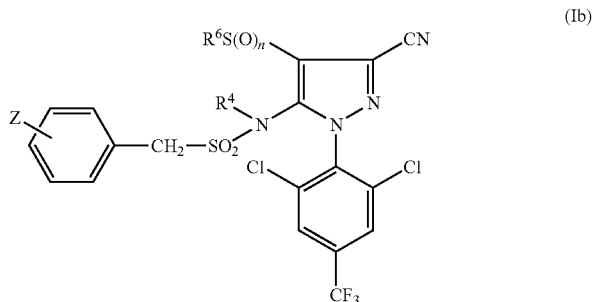

| Compound Number | R6 | R4 | Z | n | m.p. (° C.) |
|---|---|---|---|---|---|
| 3-155 | CHClCF3 | CH3 | H | 2 | |
| 3-156 | CFHCF2H | CH3 | H | 2 | |
| 3-157 | CFHCFH2 | CH3 | H | 2 | |

TABLE 4

Compounds of formula (Ic)

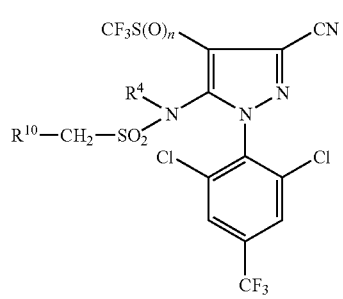

| Compound Number | R10 | R4 | n | m.p. (° C.) |
|---|---|---|---|---|
| 4-1 | 2-pyridyl | CH3 | 1 | |
| 4-2 | 3-pyridyl | CH3 | 1 | |
| 4-3 | 5-Cl-3-pyridyl | CH3 | 1 | |
| 4-4 | 4-pyridyl | CH3 | 1 | |
| 4-5 | 1-pyrimidyl | CH3 | 1 | |
| 4-6 | 3-pyrimidyl | CH3 | 1 | |
| 4-7 | 4-pyrimidyl | CH3 | 1 | |
| 4-8 | 2-thienyl | CH3 | 1 | |
| 4-9 | 3-thienyl | CH3 | 1 | |
| 4-10 | 2-furyl | CH3 | 1 | |
| 4-11 | 3-furyl | CH3 | 1 | |
| 4-12 | 2-tetrahydrofuryl | CH3 | 1 | |
| 4-13 | 3-tetrahydrofuryl | CH3 | 1 | |
| 4-14 | 3-pyrazolyl | CH3 | 1 | |
| 4-15 | 4-pyrazolyl | CH3 | 1 | |
| 4-16 | 5-pyrazolyl | CH3 | 1 | |
| 4-17 | 2-imidazolyl | CH3 | 1 | |
| 4-18 | 4-imidazolyl | CH3 | 1 | |
| 4-19 | 5-imidazolyl | CH3 | 1 | |
| 4-20 | 2-thiazolyl | CH3 | 1 | |
| 4-21 | 4-thiazolyl | CH3 | 1 | |
| 4-22 | 5-thiazolyl | CH3 | 1 | |

TABLE 4-continued

Compounds of formula (Ic)

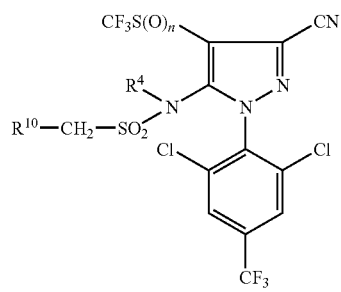

| Compound Number | R10 | R4 | n | m.p. (° C.) |
|---|---|---|---|---|
| 4-23 | 2-tetrahydrothienyl | CH3 | 1 | |
| 4-24 | 2-pyrrolyl | CH3 | 1 | |
| 4-25 | 3-pyrrolyl | CH3 | 1 | |
| 4-26 | 4-pyrrolyl | CH3 | 1 | |
| 4-27 | 1-tetrazolyl | CH3 | 1 | |
| 4-29 | 5-tetrazolyl | CH3 | 1 | |
| 4-30 | 3-(1,2,4)-triazolyl | CH3 | 1 | |
| 4-31 | 5-(1,2,4)-triazolyl | CH3 | 1 | |
| 4-32 | 5-Cl-2-thienyl | CH3 | 0 | |
| 4-33 | 2-thienyl | CH3 | 0 | |
| 4-34 | 2-thienyl | CH3 | 2 | |
| 4-35 | 5-Cl-2-thienyl | CH3 | 1 | |

TABLE 5

Compounds of formula (Id)

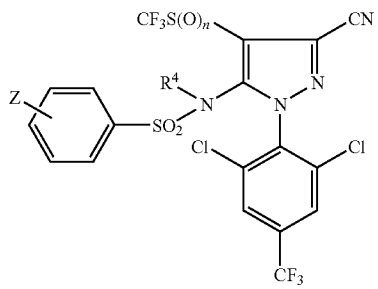
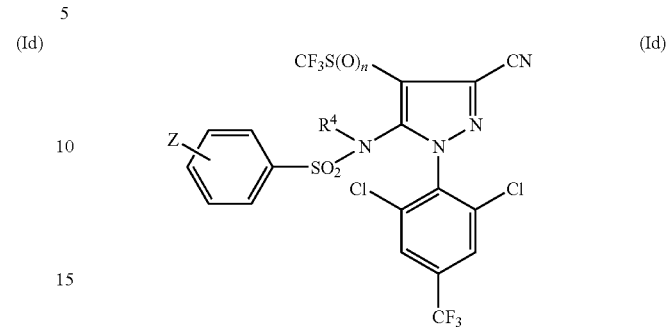

| Compound Number | R⁴ | Z | n | m.p. (° C.)/ 1HNMR NCH3 |
|---|---|---|---|---|
| 5-1 | CH3 | 2-Cl | 0 | |
| 5-2 | CH3 | 3-Cl | 0 | |
| 5-3 | CH3 | 4-Cl | 0 | 177 |
| 5-4 | CH3 | 2,5-Cl2 | 0 | |
| 5-5 | CH3 | 2,6-Cl2 | 0 | |
| 5-6 | CH3 | 3,4-Cl2 | 0 | |
| 5-7 | CH3 | 2-F | 0 | |
| 5-8 | CH3 | 3-F | 0 | |
| 5-9 | CH3 | 4-F | 0 | 153 |
| 5-10 | CH3 | 3,4-F2 | 0 | |
| 5-11 | CH3 | 2,6-F2 | 0 | |
| 5-12 | CH3 | 4-Br | 0 | |
| 5-13 | CH3 | 4-I | 0 | |
| 5-14 | CH3 | 2-CF3 | 0 | |
| 5-15 | CH3 | 3-CF3 | 0 | 167 |
| 5-16 | CH3 | 4-CF3 | 0 | 158 |
| 5-17 | CH3 | 3,5-(CF3)2 | 0 | |
| 5-18 | CH3 | 4-CF3, 2-Cl | 0 | |
| 5-19 | CH3 | 3-CF3, 4-Cl | 0 | |
| 5-20 | CH3 | 2-OCH3 | 0 | |
| 5-21 | CH3 | 3-OCH3 | 0 | |
| 5-22 | CH3 | 4-OCH3 | 0 | 152 |
| 5-23 | CH3 | 4-SCH3 | 0 | |
| 5-24 | CH3 | 4-SCF3 | 0 | |
| 5-25 | CH3 | 4-SF5 | 0 | |
| 5-26 | CH3 | 3,4-(OCH3)2 | 0 | |
| 5-27 | CH3 | 4-Ph | 0 | |
| 5-28 | CH3 | 4-I | 0 | |
| 5-29 | CH3 | 2-CH3 | 0 | |
| 5-30 | CH3 | 3-CH3 | 0 | 105 |
| 5-31 | CH3 | 2,3-(CH3)2 | 0 | |
| 5-32 | CH3 | 4-CH3 | 0 | 154 |
| 5-33 | CH3 | 2,5-(CH3)2 | 0 | |
| 5-34 | CH3 | 2,6-(CH3)2 | 0 | |
| 5-35 | CH3 | 3,4-(CH3)2 | 0 | |
| 5-36 | CH3 | H | 0 | 112 |
| 5-37 | CH3 | 4-OCF3 | 0 | 141 |
| 5-38 | CH3 | t-C4H9 | 0 | 170 |
| 5-39 | CH3 | 2,4,6-Cl3 | 0 | |
| 5-40 | CH3 | 2,4,6-(CH3)3- | 0 | 135 |
| 5-41 | CH3 | 2-CO2CH3,5-I | 0 | |
| 5-42 | CH3 | 3,5-Cl2 | 0 | 138 |
| 5-43 | CH3 | 4-NO2 | 0 | |
| 5-44 | CH3 | 1-naphthyl | 0 | 131 |
| 5-45 | CH3 | 2,6-Cl2,4-CF3 | 0 | |
| 5-46 | CH3 | 2-Cl | 1 | 195 |
| 5-47 | CH3 | 3-Cl | 1 | 129 |
| 5-48 | CH3 | 4-Cl | 1 | 131 |
| 5-49 | CH3 | 2,5-Cl2 | 1 | 180 |
| 5-50 | CH3 | 2,6-Cl2 | 1 | |
| 5-51 | CH3 | 3,4-Cl2 | 1 | |
| 5-52 | CH3 | 2-F | 1 | |
| 5-53 | CH3 | 3-F | 1 | |
| 5-54 | CH3 | 4-F | 1 | 144 |
| 5-55 | CH3 | 3,4-F2 | 1 | |
| 5-56 | CH3 | 2,6-F2 | 1 | |
| 5-57 | CH3 | 4-Br | 1 | |
| 5-58 | CH3 | 4-I | 1 | |
| 5-59 | CH3 | 2-CF3 | 1 | |
| 5-60 | CH3 | 3-CF3 | 1 | 161 |
| 5-61 | CH3 | 4-CF3 | 1 | 138 |
| 5-62 | CH3 | 3,5-(CF3)2 | 1 | |
| 5-63 | CH3 | 4-CF3, 2-Cl | 1 | |
| 5-64 | CH3 | 3-CF3, 4-Cl | 1 | |
| 5-65 | CH3 | 2-OCH3 | 1 | wax |
| 5-66 | CH3 | 3-OCH3 | 1 | |
| 5-67 | CH3 | 4-OCH3 | 1 | |
| 5-68 | CH3 | 4-SCH3 | 1 | |
| 5-69 | CH3 | 4-SCF3 | 1 | |
| 5-70 | CH3 | 4-SF5 | 1 | |
| 5-71 | CH3 | 3,4-(OCH3)2 | 1 | |
| 5-72 | CH3 | 4-Ph | 1 | |
| 5-73 | CH3 | 4-I | 1 | |
| 5-74 | CH3 | 2-CH3 | 1 | |
| 5-75 | CH3 | 3-CH3 | 1 | 3.24s,3H |
| 5-76 | CH3 | 2,3-(CH3)2 | 1 | |
| 5-77 | CH3 | 4-CH3 | 1 | |
| 5-78 | CH3 | 2,5-(CH3)2 | 1 | |
| 5-79 | CH3 | 2,6-(CH3)2 | 1 | |
| 5-80 | CH3 | 3,4-(CH3)2 | 1 | |
| 5-81 | CH3 | H | 1 | 161 |
| 5-82 | CH3 | 4-OCF3 | 1 | 96 |
| 5-83 | CH3 | t-C4H9 | 1 | 74 |
| 5-84 | CH3 | 2,4,6-Cl3 | 1 | 168 |
| 5-85 | CH3 | 2,4,6-(CH3)3 | 1 | 147 |
| 5-86 | CH3 | 2-CO2CH3,5-I | 1 | 3.40s,3H |
| 5-87 | CH3 | 3,5-Cl2 | 1 | 131 |
| 5-88 | CH3 | 4-NO2 | 1 | 194 |
| 5-89 | CH3 | 1-naphthyl | 1 | 140 |
| 5-90 | CH3 | 2,6-Cl2,4-CF3 | 1 | |
| 5-91 | CH3 | 2-Cl | 2 | |
| 5-92 | CH3 | 3-Cl | 2 | |
| 5-93 | CH3 | 4-Cl | 2 | |
| 5-94 | CH3 | 2,5-Cl2 | 2 | |
| 5-95 | CH3 | 2,6-Cl2 | 2 | |
| 5-96 | CH3 | 3,4-Cl2 | 2 | |
| 5-97 | CH3 | 2-F | 2 | |
| 5-98 | CH3 | 3-F | 2 | |
| 5-99 | CH3 | 4-F | 2 | |
| 5-100 | CH3 | 3,4-F2 | 2 | |
| 5-101 | CH3 | 2,6-F2 | 2 | |
| 5-102 | CH3 | 4-Br | 2 | |
| 5-103 | CH3 | 4-I | 2 | |
| 5-104 | CH3 | 2-CF3 | 2 | 171 |
| 5-105 | CH3 | 3-CF3 | 2 | |
| 5-106 | CH3 | 4-CF3 | 2 | |
| 5-107 | CH3 | 3,5-(CF3)2 | 2 | |
| 5-108 | CH3 | 4-CF3, 2-Cl | 2 | |
| 5-109 | CH3 | 3-CF3, 4-Cl | 2 | |
| 5-110 | CH3 | 2-OCH3 | 2 | |
| 5-111 | CH3 | 3-OCH3 | 2 | |
| 5-112 | CH3 | 4-OCH3 | 2 | |

TABLE 5-continued

Compounds of formula (Id)

(Id)

| Compound Number | R⁴ | Z | n | m.p. (° C.)/ 1HNMR NCH3 |
|---|---|---|---|---|
| 5-113 | CH3 | 4-SCH3 | 2 | |
| 5-114 | CH3 | 4-SCF3 | 2 | |
| 5-115 | CH3 | 4-SF5 | 2 | |
| 5-116 | CH3 | 3,4-(OCH3)2 | 2 | |
| 5-117 | CH3 | 4-Ph | 2 | |
| 5-118 | CH3 | 4-I | 2 | |
| 5-119 | CH3 | 2-CH3 | 2 | |
| 5-120 | CH3 | 3-CH3 | 2 | |
| 5-121 | CH3 | 2,3-(CH3)2 | 2 | |
| 5-122 | CH3 | 4-CH3 | 2 | |
| 5-123 | CH3 | 2,5-(CH3)2 | 2 | |
| 5-124 | CH3 | 2,6-(CH3)2 | 2 | |
| 5-125 | CH3 | 3,4-(CH3)2 | 2 | |
| 5-126 | CH3 | H | 2 | |
| 5-127 | CH3 | 4-OCF3 | 2 | |
| 5-128 | CH3 | t-C4H9 | 2 | |
| 5-129 | CH3 | 2,4,6-Cl3 | 2 | |
| 5-130 | CH3 | 2,4,6-(CH3)3 | 2 | |
| 5-131 | CH3 | 2-CO2CH3,5-I | 2 | |
| 5-132 | CH3 | 3,5-Cl2 | 2 | |
| 5-133 | CH3 | 4-NO2 | 2 | |
| 5-134 | CH3 | 1-naphthyl | 2 | |
| 5-135 | CH3 | 2,6-Cl2,4-CF3 | 2 | |
| 5-136 | CH3 | 4-(4-F—PhO) | 1 | 147 |
| 5-137 | CH3 | 4-(3,5-Cl2—PhO) | 1 | 159 |
| 5-138 | CH3 | 4-(4-Cl—PhO) | 1 | wax |
| 5-139 | CH3 | 4-(4-CH3O—PhO) | 1 | 167 |
| 5-140 | CH3 | 4-PhO | 1 | 144 |
| 5-141 | CH3 | 4-(3,5-CF3—PhO) | 1 | |
| 5-142 | CH3 | 4-(4-CF3—PhO) | 1 | wax |
| 5-143 | CH3 | 4-(4-CH3—PhO) | 1 | 190 |
| 5-144 | CH3 | 4-(3,4-Cl2—PhO) | 1 | 158 |
| 5-145 | CH3 | 4-(2-CF3—PhO) | 1 | |
| 5-146 | CH3 | 4-(2-CH3—PhO) | 1 | |
| 5-147 | CH3 | 4-(2-OCH3—PhO) | 1 | |
| 5-148 | CH3 | 4-(2-Cl—PhO) | 1 | |
| 5-149 | CH3 | 4-(4-CF3—Ph) | 1 | 166 |
| 5-150 | CH3 | 4-(3,4-Cl2—Ph) | 1 | 102 |
| 5-151 | CH3 | 4-(4-F—Ph) | 1 | 159 |
| 5-152 | CH3 | 4-(4-CH3—Ph) | 1 | 110 |
| 5-153 | CH3 | 4-(2,3-Cl2—Ph) | 1 | |
| 5-154 | CH3 | 4-(4-OCH3—Ph) | 1 | wax |
| 5-155 | CH3 | 4-(4,6-Cl2—Ph) | 1 | |
| 5-156 | CH3 | 4-(3,5-Cl2—Ph) | 1 | |
| 5-157 | CH3 | 2,4,5-Cl3 | 1 | |
| 5-158 | CH3 | Ph—(3,4-OCH2CH2O—) | 0 | 139 |
| 5-159 | CH3 | Ph—(3,4-OCH2CH2O—) | 1 | |
| 5-160 | CH3 | 4-C5H11 | 0 | 98 |
| 5-161 | CH3 | 4-C5H11 | 1 | 104 |
| 5-162 | CH3 | 4-(4-Cl—Ph) | 1 | wax |
| 5-163 | CH3 | 4-[3,5-(CF3)2—Ph] | 1 | 145 |
| 5-164 | CH3 | 2-OCH3, 5-Br | 1 | 197 |
| 5-165 | CH3 | 2-Br | 1 | wax |
| 5-166 | CH3 | 2-CN | 1 | 191 |
| 5-167 | CH3 | 2-OCH3, 5-Cl | 1 | 178 |
| 5-168 | CH3 | 2,6-(CH3)2,4-isopropyl | 1 | 170 |
| 5-169 | CH3 | 6-Coumaryl | 1 | >235 |
| 5-170 | CH3 | 2-CH=N—O—CH3 | 1 | 146 |
| 5-171 | CH3 | 2,3-(CH3)2, 5-t-C4H9 | 1 | 210 |
| 5-172 | CH3 | 2-Ph | 1 | wax |
| 5-173 | CH3 | 2-OCH3, 6-Cl | 1 | oil |
| 5-174 | CH3 | 4-CH(CH3)CH2CH3 | 1 | 145 |
| 5-175 | CH3 | 2-Cl, 4-CH3 | 1 | 98 |
| 5-176 | CH3 | 2-CH3, 4-Cl | 1 | 106 |
| 5-177 | CH3 | 2,4-(isopropyl)2 | 1 | oil |
| 5-178 | CH3 | 2,4-CH2CH3 | 1 | 73 |
| 5-179 | CH3 | 2,5-(isopropyl)2 | 1 | oil |
| 5-180 | CH3 | 2-CH3, 3,5-Cl2 | 1 | 97 |
| 5-181 | CH3 | 2-OCH2CH3, 5-isopropyl | 1 | 97 |
| 5-182 | CH3 | 2-Cl, 3,5-(CH3)2 | 1 | 95 |
| 5-183 | CH3 | 3-F, 5-CH3 | 1 | 175 |
| 5-184 | CH3 | 2-F, 5-OCH3 | 1 | 173 |
| 5-185 | CH3 | 2-C(O)OPh | 1 | 57 |
| 5-186 | CH3 | 2-OCH2CH2CH3, 6-CH3 | 1 | 101 |
| 5-187 | CH3 | 3-NO2, 4-OCF3 | 1 | 98 |
| 5-188 | CH3 | 4-O-pyrid-2-yl | 1 | 116 |
| 5-189 | CH3 | 2-S—Ph | 1 | 179 |
| 5-190 | CH3 | 2-C(O)OCH2CF3, 5-CH3 | 1 | oil |
| 5-191 | CH3 | 2-C(O)OCH2CH2OCH3 | 1 | 135 |

TABLE 6

Compounds of formula (Ie)

(Ie)

| Compound Number | R⁴ | Z | n | m.p. (° C.) |
|---|---|---|---|---|
| 6-1 | H | H | 0 | |
| 6-2 | CH3 | H | 0 | |
| 6-3 | CH2CH3 | H | 0 | |
| 6-4 | CH2CH2CH3 | H | 0 | |
| 6-5 | CH2CH2CH2CH3 | H | 0 | |
| 6-6 | CH2CHCH2 | H | 0 | |
| 6-7 | CH2CCH | H | 0 | |

TABLE 6-continued

Compounds of formula (Ie)

(Ie)

| Compound Number | R⁴ | Z | n | m.p. (° C.) |
|---|---|---|---|---|
| 6-8 | C(O)OCH3 | H | 0 | |
| 6-9 | C(O)OCH2CH3 | H | 0 | |
| 6-10 | CH2OCH3 | H | 0 | |
| 6-11 | CH2OCH2CH3 | H | 0 | |
| 6-12 | CH2cyclopropyl | H | 0 | |
| 6-13 | cyclopropyl | H | 0 | |
| 6-14 | CH2Ph | H | 0 | |
| 6-15 | H | H | 1 | |
| 6-16 | CH3 | H | 1 | |
| 6-17 | CH2CH3 | H | 1 | |
| 6-18 | CH2CH2CH3 | H | 1 | |
| 6-19 | CH2CH2CH2CH3 | H | 1 | |
| 6-20 | CH2CHCH2 | H | 1 | |
| 6-21 | CH2CCH | H | 1 | |
| 6-22 | C(O)OCH3 | H | 1 | |
| 6-23 | C(O)OCH2CH3 | H | 1 | |
| 6-24 | CH2OCH3 | H | 1 | |
| 6-25 | CH2OCH2CH3 | H | 1 | |
| 6-26 | CH2cyclopropyl | H | 1 | |
| 6-27 | cyclopropyl | H | 1 | |
| 6-28 | CH2Ph | H | 1 | |
| 6-29 | H | H | 2 | |
| 6-30 | CH3 | H | 2 | |
| 6-31 | CH2CH3 | H | 2 | |
| 6-32 | CH2CH2CH3 | H | 2 | |
| 6-33 | CH2CH2CH2CH3 | H | 2 | |
| 6-34 | CH2CHCH2 | H | 2 | |
| 6-35 | CH2CCH | H | 2 | |
| 6-36 | C(O)OCH3 | H | 2 | |
| 6-37 | C(O)OCH2CH3 | H | 2 | |
| 6-38 | CH2OCH3 | H | 2 | |
| 6-39 | CH2OCH2CH3 | H | 2 | |
| 6-40 | CH2cyclopropyl | H | 2 | |
| 6-41 | cyclopropyl | H | 2 | |
| 6-42 | CH2Ph | H | 2 | |
| 6-43 | CH3 | 2-Cl | 0 | |
| 6-44 | CH3 | 3-Cl | 0 | |
| 6-45 | CH3 | 4-Cl | 0 | |
| 6-46 | CH3 | 2,5-Cl2 | 0 | |
| 6-47 | CH3 | 2,6-Cl2 | 0 | |
| 6-48 | CH3 | 3,4-Cl2 | 0 | |
| 6-49 | CH3 | 2-F | 0 | |
| 6-50 | CH3 | 3-F | 0 | |
| 6-51 | CH3 | 4-F | 0 | |
| 6-52 | CH3 | 3,4-F2 | 0 | |
| 6-53 | CH3 | 2,6-F2 | 0 | |
| 6-54 | CH3 | 4-Br | 0 | |
| 6-55 | CH3 | 4-I | 0 | |
| 6-56 | CH3 | 2-CF3 | 0 | |
| 6-57 | CH3 | 3-CF3 | 0 | |
| 6-58 | CH3 | 4-CF3 | 0 | |
| 6-59 | CH3 | 3,5-(CF3)2 | 0 | |
| 6-60 | CH3 | 4-CF3, 2-Cl | 0 | |
| 6-61 | CH3 | 3-CF3, 4-Cl | 0 | |
| 6-62 | CH3 | 2-OCH3 | 0 | |
| 6-63 | CH3 | 3-OCH3 | 0 | |
| 6-64 | CH3 | 4-OCH3 | 0 | |
| 6-65 | CH3 | 4-SCH3 | 0 | |
| 6-66 | CH3 | 4-SCF3 | 0 | |
| 6-67 | CH3 | 4-SF5 | 0 | |
| 6-68 | CH3 | 3,4-(OCH3)2 | 0 | |
| 6-69 | CH3 | 4-Ph | 0 | |
| 6-70 | CH3 | 4-I | 0 | |
| 6-71 | CH3 | 2-CH3 | 0 | |
| 6-72 | CH3 | 3-CH3 | 0 | |
| 6-73 | CH3 | 2,3-(CH3)2 | 0 | |
| 6-74 | CH3 | 4-CH3 | 0 | |
| 6-75 | CH3 | 2,5-(CH3)2 | 0 | |
| 6-76 | CH3 | 2,6-(CH3)2 | 0 | |
| 6-77 | CH3 | 3,4-(CH3)2 | 0 | |
| 6-78 | CH3 | 2-Cl | 1 | |
| 6-79 | CH3 | 3-Cl | 1 | |
| 6-80 | CH3 | 4-Cl | 1 | |
| 6-81 | CH3 | 2,5-Cl2 | 1 | |
| 6-82 | CH3 | 2,6-Cl2 | 1 | |
| 6-83 | CH3 | 3,4-Cl2 | 1 | |
| 6-84 | CH3 | 2-F | 1 | |
| 6-85 | CH3 | 3-F | 1 | |
| 6-86 | CH3 | 4-F | 1 | |
| 6-87 | CH3 | 3,4-F2 | 1 | |
| 6-88 | CH3 | 2,6-F2 | 1 | |
| 6-89 | CH3 | 4-Br | 1 | |
| 6-90 | CH3 | 4-I | 1 | |
| 6-91 | CH3 | 2-CF3 | 1 | |
| 6-92 | CH3 | 3-CF3 | 1 | |
| 6-93 | CH3 | 4-CF3 | 1 | |
| 6-94 | CH3 | 3,5-(CF3)2 | 1 | |
| 6-95 | CH3 | 4-CF3,2-Cl | 1 | |
| 6-96 | CH3 | 3-CF3,4-Cl | 1 | |
| 6-97 | CH3 | 2-OCH3 | 1 | |
| 6-98 | CH3 | 3-OCH3 | 1 | |
| 6-99 | CH3 | 4-OCH3 | 1 | |
| 6-100 | CH3 | 4-SCH3 | 1 | |
| 6-101 | CH3 | 4-SCF3 | 1 | |
| 6-102 | CH3 | 4-SF5 | 1 | |
| 6-103 | CH3 | 3,4-(OCH3)2 | 1 | |
| 6-104 | CH3 | 4-Ph | 1 | |
| 6-105 | CH3 | 4-I | 1 | |
| 6-106 | CH3 | 2-CH3 | 1 | |
| 6-107 | CH3 | 3-CH3 | 1 | |
| 6-108 | CH3 | 2,3-(CH3)2 | 1 | |
| 6-109 | CH3 | 4-CH3 | 1 | |
| 6-110 | CH3 | 2,5-(CH3)2 | 1 | |
| 6-111 | CH3 | 2,6-(CH3)2 | 1 | |
| 6-112 | CH3 | 3,4-(CH3)2 | 1 | |
| 6-113 | CH3 | 2-Cl | 2 | |
| 6-114 | CH3 | 3-Cl | 2 | |
| 6-115 | CH3 | 4-Cl | 2 | |
| 6-116 | CH3 | 2,5-Cl2 | 2 | |
| 6-117 | CH3 | 2,6-Cl2 | 2 | |
| 6-118 | CH3 | 3,4-Cl2 | 2 | |
| 6-119 | CH3 | 2-F | 2 | |
| 6-120 | CH3 | 3-F | 2 | |
| 6-121 | CH3 | 4-F | 2 | |

TABLE 6-continued

Compounds of formula (Ie)

$$\text{(Ie)}$$

| Compound Number | R⁴ | Z | n | m.p. (° C.) |
|---|---|---|---|---|
| 6-122 | CH3 | 3,4-F2 | 2 | |
| 6-123 | CH3 | 2,6-F2 | 2 | |
| 6-124 | CH3 | 4-Br | 2 | |
| 6-125 | CH3 | 4-I | 2 | |
| 6-126 | CH3 | 2-CF3 | 2 | |
| 6-127 | CH3 | 3-CF3 | 2 | |
| 6-128 | CH3 | 4-CF3 | 2 | |
| 6-129 | CH3 | 3,5-(CF3)2 | 2 | |
| 6-130 | CH3 | 4-CF3, 2-Cl | 2 | |
| 6-131 | CH3 | 3-CF3, 4-Cl | 2 | |
| 6-132 | CH3 | 2-OCH3 | 2 | |
| 6-133 | CH3 | 3-OCH3 | 2 | |
| 6-134 | CH3 | 4-OCH3 | 2 | |
| 6-135 | CH3 | 4-SCH3 | 2 | |
| 6-136 | CH3 | 4-SCF3 | 2 | |
| 6-137 | CH3 | 4-SF5 | 2 | |
| 6-138 | CH3 | 3,4-(OCH3)2 | 2 | |
| 6-139 | CH3 | 4-Ph | 2 | |
| 6-140 | CH3 | 4-I | 2 | |
| 6-141 | CH3 | 2-CH3 | 2 | |
| 6-142 | CH3 | 3-CH3 | 2 | |
| 6-143 | CH3 | 2,3-(CH3)2 | 2 | |
| 6-144 | CH3 | 4-CH3 | 2 | |
| 6-145 | CH3 | 2,5-(CH3)2 | 2 | |
| 6-146 | CH3 | 2,6-(CH3)2 | 2 | |
| 6-147 | CH3 | 3,4-(CH3)2 | 2 | |

TABLE 7

Compounds of formula (I) in which R¹ is CSNH₂; R² is Cl; W is C—Cl; R³ is CF₃ and R⁶ is CF₃.

| Compound Number | R⁴ | R⁵ | n | m. p. (° C.) |
|---|---|---|---|---|
| 7-1 | CH3 | iPr | 1 | |
| 7-2 | CH3 | CH2CH2CH3 | 1 | |
| 7-3 | CH3 | CH2CH2CH2CH3 | 1 | |
| 7-4 | CH3 | CHCl2 | 1 | |
| 7-5 | CH3 | CH2Cl | 1 | |
| 7-6 | CH3 | CF3 | 1 | |
| 7-8 | CH3 | CFH2 | 1 | |
| 7-9 | CH3 | CF2H | 1 | |
| 7-10 | CH3 | C8H17 | 1 | |
| 7-11 | CH3 | C9H19 | 1 | |
| 7-11 | CH3 | C10H21 | 1 | |
| 7-12 | CH3 | C12H25 | 1 | |
| 7-13 | CH3 | CHCH2 | 1 | |
| 7-14 | CH3 | CH2CHCH2 | 1 | |
| 7-15 | CH3 | cyclo-C5H9 | 1 | |
| 7-16 | CH3 | cyclo-C6H11 | 1 | |
| 7-17 | CH3 | CH2CH2CH2Cl | 1 | |
| 7-18 | CH3 | CH2SO2CH3 | 1 | |
| 7-19 | CH3 | CH2NH2 | 1 | |
| 7-20 | CH3 | CH2NHCH3 | 1 | |
| 7-21 | CH3 | CH2N(CH3)2 | 1 | |
| 7-22 | CH3 | CH2NHCH2CH3 | 1 | |
| 7-23 | CH3 | CH2N(CH2CH3)2 | 1 | |
| 7-24 | CH3 | CH2CH2N(CH3)2 | 1 | |
| 7-25 | CH3 | CH2CH2N(CH2CH3)2 | 1 | |
| 7-26 | CH3 | CH2-N-morpholinyl | 1 | |
| 7-27 | CH3 | CH2OCH3 | 1 | |
| 7-28 | CH3 | CH2OCH2CH3 | 1 | |
| 7-29 | CH3 | CH2SCH3 | 1 | |
| 7-30 | CH3 | CH3 | 1 | |
| 7-31 | CH3 | CH2CH3 | 1 | |
| 7-32 | CH3 | CH2Ph | 1 | 134 |

TABLE 8

Compounds of formula (If)

$$\text{(If)}$$

| Compound Number | R¹⁰ | R⁴ | n | m.p. (° C.) |
|---|---|---|---|---|
| 8-1 | 2-pyridyl | CH3 | 1 | |
| 8-2 | 3-pyridyl | CH3 | 1 | |
| 8-3 | 5-Cl-3-pyridyl | CH3 | 1 | |
| 8-4 | 4-pyridyl | CH3 | 1 | |
| 8-5 | 1-pyrimidyl | CH3 | 1 | |
| 8-6 | 3-pyrimidyl | CH3 | 1 | |
| 8-7 | 4-pyrimidyl | CH3 | 1 | |
| 8-8 | 2-thienyl | CH3 | 1 | 138 |
| 8-9 | 3-thienyl | CH3 | 1 | |
| 8-10 | 2-furyl | CH3 | 1 | |
| 8-11 | 3-furyl | CH3 | 1 | |
| 8-12 | 2-tetrahydrofuryl | CH3 | 1 | |
| 8-13 | 3-tetrahydrofuryl | CH3 | 1 | |
| 8-14 | 3-pyrazolyl | CH3 | 1 | |
| 8-15 | 4-pyrazolyl | CH3 | 1 | |
| 8-16 | 5-pyrazolyl | CH3 | 1 | |
| 8-17 | 2-imidazolyl | CH3 | 1 | |
| 8-18 | 4-imidazolyl | CH3 | 1 | |
| 8-19 | 5-imidazolyl | CH3 | 1 | |
| 8-20 | 2-thiazolyl | CH3 | 1 | |
| 8-21 | 4-thiazolyl | CH3 | 1 | |
| 8-22 | 5-thiazolyl | CH3 | 1 | |
| 8-23 | 2-tetrahydrothienyl | CH3 | 1 | |
| 8-24 | 2-pyrrolyl | CH3 | 1 | |
| 8-25 | 3-pyrrolyl | CH3 | 1 | |
| 8-26 | 4-pyrrolyl | CH3 | 1 | |
| 8-27 | 1-tetrazolyl | CH3 | 1 | |
| 8-28 | 5-tetrazolyl | CH3 | 1 | |
| 8-29 | 3-(1,2,4)-triazolyl | CH3 | 1 | |
| 8-30 | 5-(1,2,4)-triazolyl | CH3 | 1 | |
| 8-31 | 5-Cl-2-thienyl | CH3 | 0 | |
| 8-32 | 2-thienyl | CH3 | 0 | |
| 8-33 | 2-thienyl | CH3 | 2 | |
| 8-34 | 5-Cl-2-thienyl | CH3 | 1 | 171 |

TABLE 8-continued

Compounds of formula (If)

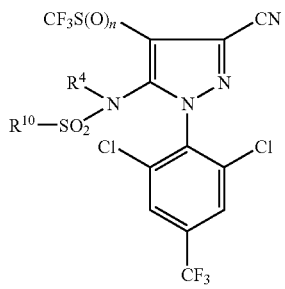

(If)

| Compound Number | R¹⁰ | R⁴ | n | m.p. (° C.) |
|---|---|---|---|---|
| 8-35 | 1-methyl-4-imidazolyl | CH3 | 0 | |
| 8-36 | 1-methyl-4-imidazolyl | CH3 | 1 | |
| 8-37 | 1,3-dimethyl-5-Cl-pyrazolyl | CH3 | 0 | 150 |
| 8-38 | 2,4-dimethyl-5-thiazolyl | CH3 | 1 | 149 |
| 8-39 | 5-(2-pyridyl)-2-thienyl | CH3 | 1 | 176 |
| 8-40 | 2-methyl-5-CF3-4-furyl | CH3 | 1 | 161 |
| 8-41 | 2,5-dimethyl-3-thienyl | CH3 | 1 | 134 |

TABLE 8-continued

Compounds of formula (If)

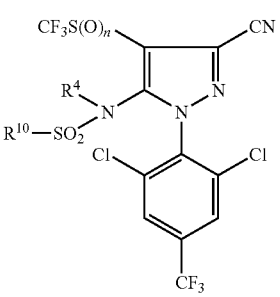

(If)

| Compound Number | R¹⁰ | R⁴ | n | m.p. (° C.) |
|---|---|---|---|---|
| 8-42 | tetradecyl | CH3 | 1 | wax |
| 8-43 | cyclopropyl | CH3 | 1 | 227 |
| 8-44 | CH2Br | CH3 | 1 | oil |
| 8-45 | CH2CH2CH2CF2CF3 | CH3 | 1 | 161 |
| 8-46 | 2-Cl-3-pyridyl | CH3 | 1 | 92 |

TABLE 9

Compounds of formula (Id)

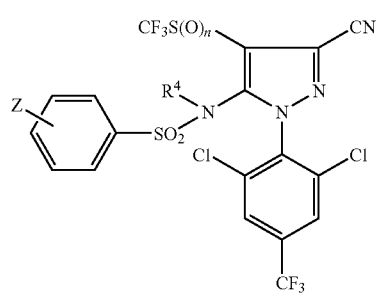

(Id)

| Compound Number | R⁴ | Z | n | m.p. (° C.)/ 1H-NMR |
|---|---|---|---|---|
| 9-1 | CH3 | 4-(Ph-4-OCH3) | 1 | 3.21s, 3H, N—CH3 |
| 9-2 | CH3 | 4-(Ph-4-Cl) | 1 | 3.25s, 3H, N—CH3 |
| 9-3 | CH3 | 4-(Ph-3,4-(Cl)2) | 1 | 102 |
| 9-4 | CH3 | 4-(Ph-4-F) | 1 | 159 |
| 9-5 | CH3 | 4-(Ph-4-CH3) | 1 | 110 |
| 9-6 | CH3 | 4-(Ph-4-CF3) | 1 | 166 |
| 9-7 | CH3 | 4-(Ph-3,5-bis-CF3) | 1 | 145 |
| 9-8 | CH3 | 4-OPh | 1 | 144 |
| 9-9 | CH3 | 4-(OPh-4-OCH3) | 1 | 167 |
| 9-10 | CH3 | O-(Ph-4-Cl) | 1 | 3.22s, 3H, N—CH3 |
| 9-11 | CH3 | 4-(OPh-3,5-(Cl)2 | 1 | 159 |
| 9-12 | CH3 | 4-(OPh-3,4-(Cl)2) | 1 | 158 |
| 9-13 | CH3 | 4-(OPh-4-F) | 1 | 147 |
| 9-14 | CH3 | 4-(OPh-4-CH3) | 1 | 190 |
| 9-15 | CH3 | 4-(OPh-4-CF3) | 1 | 3.30s, 3H, N—CH3 |
| 9-16 | CH3 | 4-OCF3 | 1 | 96 |
| 9-17 | CH3 | 2-OCH3-5-Br | 1 | 197 |
| 9-18 | CH3 | 2-Br | 1 | 3.52s, 3H, N—CH3 |
| 9-19 | CH3 | 2-CN | 1 | 191 |
| 9-20 | CH3 | 2-OCH3-5-Cl | 1 | 178 |
| 9-21 | CH3 | 2,6-Di-CH3-4-iso-propyl | 1 | 170 |
| 9-22 | CH3 | 6-Chromen-2-on | 1 | >235 |
| 9-23 | CH3 | 2-CH=N—O—CH3 | 1 | 146 |
| 9-24 | CH3 | 2,3-di-CH3-5-tert Butyl | 1 | 210 |

TABLE 9-continued

Compounds of formula (Id)

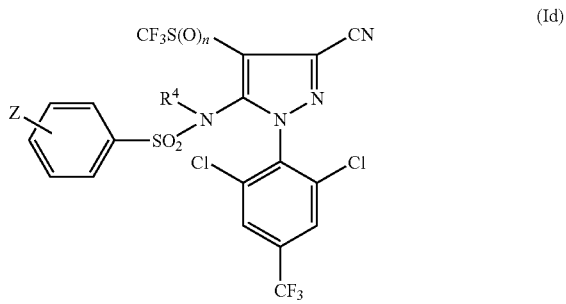

| Compound Number | R⁴ | Z | n | m.p. (° C.)/ 1H-NMR |
|---|---|---|---|---|
| 9-25 | CH3 | 2-Ph | 1 | 2.94s, 3H, N—CH3 |
| 9-26 | CH3 | 2-OCH3-6-Cl | 1 | 3.42s, 3H, N—CH3 |
| 9-27 | CH3 | 4-CH(CH3)—CH2—CH3 | 1 | 145 |
| 9-28 | CH3 | 2-Cl 4-CH3 | 1 | 98 |
| 9-29 | CH3 | 2-CH2 4-Cl | 1 | 106 |
| 9-30 | CH3 | 2,4-CH(CH3)—CH3 | 1 | 3.26s, 3H, N—CH3 |
| 9-31 | CH3 | 2,4-CH2—CH3 | 1 | 73 |
| 9-32 | CH3 | 2,5-CH(CH3)—CH3 | 1 | 3.28s, 3H, N—CH3 |
| 9-33 | CH3 | 2-CH3 3,5-Cl | 1 | 97 |
| 9-34 | CH3 | 2-OCH3 | 1 | 174 |
| 9-35 | CH3 | 2-OCH2CH3 5-CH(CH3)—CH3 | 1 | 97 |
| 9-36 | CH3 | 2-Cl 3,5-CH3 | 1 | 95 |
| 9-37 | CH3 | 3-F 5-CH3 | 1 | 175 |
| 9-38 | CH3 | 2-F 5-OCH3 | 1 | 173 |
| 9-39 | CH3 | 2-C(O)—O—Ph | 1 | 57 |
| 9-40 | CH3 | 2-OCH2CH2CH3 6-CH3 | 1 | 101 |
| 9-41 | CH3 | 3-NO2 4-OCF3 | 1 | 98 |
| 9-42 | CH3 | 4-O-pyrid-2-yl | 1 | 116 |
| 9-43 | CH3 | 2-S—Ph | 1 | 179 |
| 9-44 | CH3 | 2-C(O)OCH2CF3 5-CH3 | 1 | 2.57 d, 3H, N—CH3 |
| 9-45 | CH3 | 2-C(O)OCH2CH2OCH3 | 1 | 135 |

TABLE 10

Compounds of formula (If)

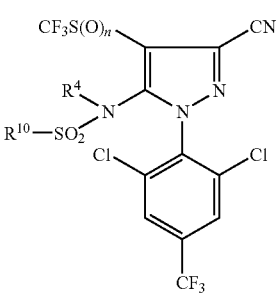

| Compound Number | R¹⁰ | R⁴ | n | m.p. (° C.)/ 1H-NMR |
|---|---|---|---|---|
| 10-1 | tetradecyl | CH3 | 1 | 3.38s, 3H, N—CH3 |
| 10-2 | cyclopropyl | CH3 | 1 | 227 |
| 10-3 | CH2—Br | CH3 | 1 | 3.51s, 3H, N—CH3 |
| 10-4 | CH2CH2CH2CF2CF3 | CH3 | 1 | 161 |
| 10-5 | 2-Cl-pyrid-3-yl | CH3 | 1 | 92 |

According to a further feature of the present invention there is provided a method for the control of pests at a locus which comprises the application of an effective amount of a compound of formula (I) or a salt thereof. For this purpose, the said compound is normally used in the form of a pesticidal composition (i.e. in association with compatible diluents or carriers and/or surface active agents suitable for use in pesticidal compositions), for example as hereinafter described.

The term "compound of the invention" as used hereinafter embraces a 5-substituted-alkylaminopyrazole of formula (I) as defined above and a pesticidally acceptable salt thereof.

One aspect of the present invention as defined above is a method for the control of pests at a locus. The locus includes, for example, the pest itself, the place (plant, field, forest, orchard, waterway, soil, plant product, or the like) where the pest resides or feeds, or a place susceptible to future infestation by the pest. The compound of the invention may therefore be applied directly to the pest, to the place where the pest resides or feeds, or to the place susceptible to future infestation by the pest. As is evident from the foregoing pesticidal uses, the present invention provides pesticidally active compounds and methods of use of said compounds for the control of a number of pest species which includes: arthropods, especially insects or arachnids, such as mites, or plant nematodes. The compound of the invention may thus be advantageously employed in practical uses, for example, in agricultural or horticultural crops, in forestry, in veterinary medicine or livestock husbandry, or in public health.

The compounds of the invention may be used for example in the following applications and on the following pests:

For the control of soil insects, such as corn rootworm, termites (especially for protection of structures), root maggots, wireworms, root weevils, stalkborers, cutworms, root aphids, or grubs. They may also be used to provide activity against plant pathogenic nematodes, such as root-knot, cyst, dagger, lesion, or stem or bulb nematodes, or against mites. For the control of soil pests, for example corn rootworm, the compounds are advantageously applied to or incorporated at an effective rate into the soil in which crops are planted or to be planted or to the seeds or growing plant roots.

In the area of public health, the compounds are especially useful in the control of many insects, especially filth flies or other Dipteran pests, such as houseflies, stableflies, soldierflies, hornflies, deerflies, horseflies, midges, punkies, blackflies, or mosquitoes.

In the protection of stored products, for example cereals, including grain or flour, groundnuts, animal feedstuffs, timber or household goods, e.g. carpets and textiles, compounds of the invention are useful against attack by arthropods, more especially beetles, including weevils, moths or mites, for example *Ephestia* spp. (flour moths), *Anthrenus* spp. (carpet beetles), *Tribolium* spp. (flour beetles), *Sitophilus* spp. (grain weevils) or *Acarus* spp. (mites).

In the control of cockroaches, ants or termites or similar arthropod pests in infested domestic or industrial premises or in the control of mosquito larvae in waterways, wells, reservoirs or other running or standing water.

For the treatment of foundations, structures or soil in the prevention of the attack on building by termites, for example, *Reticulitermes* spp., *Heterotermes* spp., *Coptotermes* spp.

In agriculture against adults, larvae and eggs of Lepidoptera (butterflies and moths), e.g. *Heliothis* spp. such as *Heliothis virescens* (tobacco budworm), *Heliothis armigera* and *Heliothis zea*. Against adults and larvae of Coleoptera (beetles) e.g. *Anthonomus* spp. e.g. grandis (cotton boll weevil), *Leptinotarsa decemlineata* (Colorado potato beetle), *Diabrotica* spp. (corn rootworms). Against Heteroptera (Hemiptera and Homoptera) e.g. *Psylla* spp., *Bernisia* spp., *Trialeurodes* spp., *Aphis* spp., *Myzus* spp., *Megoura viciae*, *Phylloxera* spp., *Nephotettix* spp. (rice leaf hoppers), *Nilaparvata* spp.

Against Diptera e.g. *Musca* spp. Against Thysanoptera such as *Thrips tabaci*.

Against Orthoptera such as *Locusta* and *Schistocerca* spp., (locusts and crickets) e.g. *Gryllus* spp., and *Acheta* spp. for example, *Blatta orientalis, Periplaneta americana, Blatella germanica, Locusta migratoria migratorioides*, and *Schistocerca gregaria*. Against Collembola e.g. *Periplaneta* spp. and *Blatella* spp. (roaches).

Against arthropods of agricultural significance such as Acari (mites) e.g. *Tetranychus* spp., and *Panonychus* spp.

Against nematodes which attack plants or trees of importance to agriculture, forestry or horticulture either directly or by spreading bacterial, viral, mycoplasma or fungal diseases of the plants. For example root-knot nematodes such as *Meloidogyne* spp. (e.g. *M. incognita*).

In the field of veterinary medicine or livestock husbandry or in the maintenance of public health against arthropods which are parasitic internally or externally upon vertebrates, particularly warm-blooded vertebrates, for example domestic animals, e.g. cattle, sheep, goats, equines, swine, poultry, dogs or cats, for example Acarina, including ticks (e.g. sotbodied ticks including *Argasidae* spp. e.g. *Argas* spp. and *Ornithodorus* spp. (e.g. *Ornithodorus moubata*); hard-bodied ticks including *Ixodidae* spp., e.g. *Boophilus* spp. e.g. *Boophilus microplus, Rhipicephalus* spp. e.g. *Rhipicephalus appendiculatus* and *Rhipicephalus sanguineus*; mites (e.g. *Damalinia* spp.); fleas (e.g. *Ctenocephalides* spp. e.g. *Ctenocephalides felis* (cat flea) and *Ctenocephalides canis* (dog flea)); lice e.g. *Menopon* spp.; Diptera (e.g. *Aedes* spp., *Anopheles* spp., *Musca* spp., *Hypoderma* spp.); Hemiptera.; Dictyoptera (e.g. *Periplaneta* spp., *Blatella* spp.); Hymenoptera; for example against infections of the gastrointestinal tract caused by parasitic nematode worms, for example members of the family Trichostrongylidae.

In a preferred aspect of the invention the compounds of formula (I) are used for the control of parasites of animals. Preferably the animal to be treated is a domestic companion animal such as a dog or a cat.

In a further aspect of the invention the compounds of formula (I) or salts or compositions thereof are used for the preparation of a veterinary medicament. In practical use for the control of arthropods, especially insects or mites, or nematode pests of plants, a method, for example, comprises applying to the plants or to the medium in which they grow an effective amount of a compound of the invention. For such a method, the compound of the invention is generally applied to the locus in which the arthropod or nematode infestation is to be controlled at an effective rate in the range of about 2 g to about 1 kg of the active compound per hectare of locus treated. Under ideal conditions, depending on the pest to be controlled, a lower rate may offer adequate protection. On the other hand, adverse weather conditions, resistance of the pest or other factors may require that the active ingredient be used at higher rates. The optimum rate depends usually upon a number of factors, for example, the type of pest being controlled, the type or the growth stage of the infested plant, the row spacing or also the method of application. Preferably an effective rate range of the active compound is from about 10 g/ha to about 400 g/ha, more preferably from about 50 g/ha to about 200 g/ha. When a pest is soil-borne, the active compound generally in a formulated composition, is distributed evenly over the area to be treated (ie, for example broadcast or band treatment) in any convenient manner and is applied at rates from about 10 g/ha to about 400 g ai/ha, preferably from about 50 g/ha to about 200 g ai/ha. When applied as a root dip to seedlings or drip irrigation to plants the liquid solution or suspension contains from about 0.075 to about 1000 mg ai/l, preferably from about 25 to about 200 mg ai/l. Application may be made, if desired, to the field or crop-growing area generally or in close proximity to the seed or plant to be protected from attack. The compound of the invention can be washed into the soil by spraying with water over the area or can be left to the natural action of rainfall. During or after application, the formulated compound can, if desired, be distributed mechanically in the soil, for example by ploughing, disking, or use of drag chains. Application can be prior to planting, at planting, after planting but before sprouting has taken place, or after sprouting.

The compound of the invention and methods of control of pests therewith are of particular value in the protection of field, forage, plantation, glasshouse, orchard or vineyard crops, of ornamentals, or of plantation or forest trees, for example: cereals (such as wheat or rice), cotton, vegetables (such as peppers), field crops (such as sugar beets, soybeans or oil seed rape), grassland or forage crops (such as maize or sorghum), orchards or groves (such as of stone or pit fruit or citrus), ornamental plants, flowers or vegetables or shrubs under glass or in gardens or parks, or forest trees (both deciduous and evergreen) in forests, plantations or nurseries.

They are also valuable in the protection of timber (standing, felled, converted, stored or structural) from attack, for example, by sawflies or beetles or termites. They have applications in the protection of stored products such as grains, fruits, nuts, spices or tobacco, whether whole, milled or compounded into products, from moth, beetle, mite or grain weevil attack. Also protected are stored animal products such as skins, hair, wool or feathers in natural or converted form (e.g. as carpets or textiles) from moth or beetle attack as well as stored meat, fish or grains from beetle, mite or fly attack.

Additionally, the compound of the invention and methods of use thereof are of particular value in the control of arthropods or helminths which are injurious to, or spread or act as vectors of diseases domestic animals, for example those hereinbefore mentioned, and more especially in the control of ticks, mites, lice, fleas, midges, or biting, nuisance or myiasis flies. The compounds of the invention are particularly useful in controlling arthropods or helminths which are present inside domestic host animals or which feed in or on the skin or suck the blood of the animal, for which purpose they may be administered orally, parenterally, percutaneously or topically.

The compositions hereinafter described for application to growing crops or crop growing loci or as a seed dressing may, in general, alternatively be employed in the protection of stored products, household goods, property or areas of the general environment. Suitable means of applying the compounds of the invention include: to growing crops as foliar sprays (for example as an in-furrow spray), dusts, granules, fogs or foams or also as suspensions of finely divided or encapsulated compositions as soil or root treatments by liquid drenches, dusts, granules, smokes or foams; to seeds of crops via application as seed dressings by liquid slurries or dusts;

to animals infested by or exposed to infestation by arthropods or helminths, by parenteral, oral or topical application of compositions in which the active ingredient exhibits an immediate and/or prolonged action over a period of time against the arthropods or helminths, for example by incorporation in feed or suitable orally-ingestible pharmaceutical formulations, edible baits, salt licks, dietary supplements, pour-on formulations, sprays, baths, dips, showers, jets, dusts, greases, shampoos, creams, wax smears or livestock self-treatment systems;

to the environment in general or to specific locations where pests may lurk, including stored products, timber, household goods, or domestic or industrial premises, as sprays, fogs, dusts, smokes, wax-smears, lacquers, granules or baits, or in tricklefeeds to waterways, wells, reservoirs or other running or standing water.

The compounds of formula (I) are particularly useful for the control of parasites of animals when applied orally, and in a further preferred aspect of the invention the compounds of formula (I) are used for the control of parasites of animals by oral application. The compounds of the formula (I) or salts thereof may be administered before, during or after meals. The compounds of the formula (I) or salts thereof may be mixed with a carrier and/or foodstuff.

The compound of the formula (I) or salt thereof is administered orally in a dose to the animal in a dose range generally from 0.1 to 500 mg/kg of the compound of the formula (I) or salt thereof per kilogram of animal body weight (mg/kg). The frequency of treatment of the animal, preferably the domestic animal to be treated by the compound of the formula (I) or salt thereof is generally from about once per week to about once per year, preferably from about once every two weeks to once every three months.

The compounds of the invention may be administered most advantageously with another parasiticidally effective material, such as an endoparasiticide, and/or an ectoparasiticide, and/or an endectoparasiticide. For example, such compounds include macrocyclic lactones such as avermectins or milbemycins e.g., ivermectin, pyratel or an insect growth regulator such as lufenuron or methoprene.

The compounds of the formula (I) can also be employed for controlling harmful organisms in crops of known genetically engineered plants or genetically engineered plants yet to be developed. As a rule, the transgenic plants are distinguished by especially advantageous properties, for example by resistances to particular crop protection agents, resistances to plant diseases or pathogens of plant diseases, such as particular insects or microorganisms such as fungi, bacteria or viruses. Other particular properties concern, for example, the harvested material with regard to quantity, quality, storage properties, composition and specific constituents. Thus, transgenic plants are known where the starch content is increased, or the starch quality is altered, or where the harvested material has a different fatty acid composition.

The use in economically important transgenic crops of useful plants and ornamentals is preferred, for example of cereals such as wheat, barley, rye, oats, millet, rice, cassaya and maize or else crops of sugar beet, cotton, soya, oilseed rape, potatoes, tomatoes, peas and other types of vegetables.

When used in transgenic crops, in particular those which have resistances to insects, effects are frequently observed, in addition to the effects against harmful organisms to be observed in other crops, which are specific for application in the transgenic crop in question, for example an altered or specifically widened spectrum of pests which can be controlled, or altered application rates which may be employed for application.

The invention therefore also relates to the use of compounds of the formula (I) for controlling harmful organisms in transgenic crop plants.

According to a further feature of the present invention there is provided a pesticidal composition comprising one or more compounds of the invention as defined above, in association with, and preferably homogeneously dispersed in one or more compatible pesticidally acceptable diluents or carriers and/or surface active agents [i.e. diluents or carriers and/or surface active agents of the type generally accepted in the art as being suitable for use in pesticidal compositions and which are compatible with compounds of the invention].

In practice, the compounds of the invention most frequently form parts of compositions. These compositions can be employed to control arthropods, especially insects and arachnids, such as mites, or helminths, such as plant nematodes. The compositions may be of any type known in the art suitable for application to the desired pest in any premises or indoor or outdoor area. These compositions contain at least one compound of the invention as the active ingredient in combination or association with one or more other compatible components which are for example, solid or liquid carriers or diluents, adjuvants, surface-active-agents, or the like appropriate for the intended use and which are agronomically or medicinally acceptable. These compositions, which may be prepared by any manner known in the art, likewise form a part of this invention.

The compounds of the invention, in their commercially available formulations and in the use forms prepared from these formulations may be present in mixtures with other active substances such as insecticides, attractants, sterilants, acaricides, nematicides, fungicides, growth regulatory substances or herbicides.

The pesticides include, for example, phosphoric esters, carbamates, carboxylic esters, formamidines, tin compounds and materials produced by microorganisms.

Preferred components in mixtures are:

1. from the group of the phosphorus compounds acephate, azamethiphos, azinphos-ethyl, azinphos-methyl, bromophos, bromophos-ethyl, cadusafos (F-67825), chlorethoxyphos, chlorfenvinphos, chlormephos, chlorpyrifos, chlorpyrifos-methyl, demeton, demeton-5-methyl, demeton-5-methyl sulfone, dialifos, diazinon, dichlorvos, dicrotophos, dimethoate, disulfoton, EPN, ethion, ethoprophos, etrimfos, famphur, fenamiphos, fenitriothion, fensulfothion, fenthion, flupyrazofos, fonofos, formothion, fosthiazate, heptenophos, isazophos, isothioate, isoxathion, malathion, methacrifos, methamidophos, methidathion, salithion, mevinphos, monocrotophos, naled, omethoate, oxydemeton-methyl, parathion, parathion-methyl, phenthoate, phorate, phosalone, phosfolan, phosphocarb (BAS-301), phosmet, phosphamidon, phoxim, pirimiphos, pirimiphos-ethyl, pirimiphos-methyl, profenofos, propaphos, proetamphos, prothiofos, pyraclofos, pyridapenthion, quinalphos, suiprofos, temephos, terbufos, tebupirimfos, tetrachlorvinphos, thiometon, triazophos, trichlorphon, vamidothion;

2. from the group of the carbamates alanycarb (OK-135), aldicarb, 2-sec-butylphenyl methylcarbamate (BPMC), carbaryl, carbofuran, carbosulfan, cloethocarb, benfuracarb, ethiofencarb, furathiocarb, HCN-801, isoprocarb, methomyl, 5-methyl-m-cumenylbutyryl (methyl) carbamate, oxamyl, pirimicarb, propoxur, thiodicarb, thiofanox, 1-methylthio(ethylideneamino)-N-methyl-N-(morpholinothio)carbamate (UC 51717), triazamate;

3. from the group of the carboxylic esters acrinathrin, allethrin, alphametrin, 5-benzyl-3-furylmethyl (E)-(1R)-cis-2,2-dimethyl-3-(2-oxothiolan-3-ylidenemethyl)cyclopropanecarboxylate, beta-cyfluthrin, alpha-cypermethrin, beta-cypermethrin, bioallethrin, bioallethrin ((S)-cyclopentylisomer), bioresmethrin, bifenthrin, (RS)-1-cyano-1-(6-phenoxy-2-pyridyl)methyl (1RS)-trans-3-(4-tert-butylphenyl)-2,2-dimethylcyclopropanecarboxylate (NCI 85193), cyloprothrin, cyfluthrin, cyhalothrin, cythithrin, cypermethrin, cyphenothrin, deltamethrin, empenthrin, esfenvalerate, fenfluthrin, fenpropathrin, fenvalerate, flucythrinate, flumethrin, fluvalinate (D isomer), imiprothrin (S41311), lambda-cyhalothrin, permethrin, phenothrin (® isomer), prallethrin, pyrethrins (natural products), resmethrin, tefluthrin, tetramethrin, theta-cypermethrin, tralomethrin, transfluthrin, zeta-cypermethrin (F-56701);

4. from the group of the amidines amitraz, chlordimeform;

5. from the group of the tin compounds cyhexatin, fenbutatin oxide;

6. others abamectin, ABG-9008, acetamiprid, acequinocyl, Anagrapha falcitera, AKD-1022, AKD-3059, ANS-118, azadirachtin, *Bacillus thuringiensis, Beauveria* bassianea, bensultap, bifenazate, binapacryl, BJL-932, bromopropylate, BTG-504, BTG-505, buprofezin, camphechlor, cartap, chlorobenzilate, chlorfenapyr, chlorfluazuron, 2-(4-chlorophenyl)-4,5-diphenylthiophene (UBI-T 930), chlorfentezine, chlorproxyfen, chromafenozide, clothianidine, 2-naphthylmethyl cyclopropanecarboxylate (Rol 2-0470), cyromazin, diacloden (thiamethoxam), diafenthiuron, DBI-3204, ethyl 2-chloro-N-(3,5-dichloro-4-(1,1,2,3,3,3-hexafluoro-1-propyloxy)phenyl) carbamoyl)-2-carboximidate, DDT, dicofol, diflubenzuron, N-(2,3-dihydro-3-methyl-1,3-thiazol-2-ylidene)-2,4-xylidine, dihydroxymethyldihydroxypyrrolidine, dinobuton, dinocap, diofenolan, emamectin benzoate, endosulfan, ethiprole (sulfethiprole), ethofenprox, etoxazole, fenazaquin, fenoxycarb, fipronil, fluazuron, flumite (flufenzine, SZI-121), 2-fluoro-5-(4-(4-ethoxyphenyl)$_4$-methyl-1-pentyl) diphenyl ether (MTI 800), granulosis and nuclear polyhedrosis viruses, fenpyroximate, fenthiocarb, fluacrypyrim, flubenzimine, flubrocythrinate, flucycloxuron, flufenoxuron, flufenzine, flufenprox, fluproxyfen, gamma-HCH, halfenozide, halofenprox, hexaflumuron (DE_473), hexythiazox, HOI-9004, hydramethylnon (AC 217300), IKI-220, indoxacarb, ivermectin, L-14165, imidacloprid, indoxacarb (DPX-MP062), kanemite (AKD-2023), lufenuron, M-020, M-020, methoxyfenozide, milbemectin, NC-196, neemgard, nidinoterfuran, nitenpyram, 2-nitromethyl-4,5-dihydro-6H-thiazine (DS 52618), 2-nitromethyl-3,4-dihydrothiazole (SD 35651), 2-nitromethylene-1,2-thiazinan-3-ylcarbamaldehyde (WNL 108477), novaluron, pirydaryl, propargite, protrifenbute, pymethrozine, pyridaben, pyrimidifen, pyriproxyfen, NC-196, NC-1111, NNI-9768, novaluron (MCW-275), OK-9701, OK-9601, OK-9602, OK-9802, R-195, RH-0345, RH-2485, RYI-210, S-1283, S-1833, SI-8601, silafluofen, silomadine (CG-177), spinosad, spirodiclofen, SU-9118, tebufenozide, tebufenpyrad, teflubenzuron, tetradifon, tetrasul, thiacloprid, thiocyclam, thiamethoxam, tolfenpyrad, triazamate, triethoxyspinosyn A, triflumuron, verbutin, vertalec (mykotal), YI-5301.

The abovementioned components for combinations are known active substances, many of which are described in Ch. R Worthing, S. B. Walker, The Pesticide Manual, 12$^{th}$ Edition, British Crop Protection Council, Farnham 2000.

The effective use doses of the compounds employed in the invention can vary within wide limits, particularly depending on the nature of the pest to be eliminated or degree of infestation, for example, of crops with these pests. In general, the compositions according to the invention usually contain about 0.05 to about 95% (by weight) of one or more active ingredients according to the invention, about 1 to about 95% of one or more solid or liquid carriers and, optionally, about 0.1 to about 50% of one or more other compatible components, such as surface-active agents or the like. In the present account, the term "carrier" denotes an organic or inorganic ingredient, natural or synthetic, with which the active ingredient is combined to facilitate its application, for example, to the plant, to seeds or to the soil. This carrier is therefore generally inert and it must be acceptable (for example, agronomically acceptable, particularly to the treated plant).

The carrier may be a solid, for example, clays, natural or synthetic silicates, silica, resins, waxes, solid fertilizers (for example ammonium salts), ground natural minerals, such as kaolins, clays, talc, chalk, quartz, attapulgite, montmorillonite, bentonite or diatomaceous earth, or ground synthetic minerals, such as silica, alumina, or silicates especially aluminium or magnesium silicates. As solid carriers for granules the following are suitable: crushed or fractionated natural rocks such as calcite, marble, pumice, sepiolite and dolomite; synthetic granules of inorganic or organic meals; granules of organic material such as sawdust, coconut shells, corn cobs, corn husks or tobacco stalks; kieselguhr, tricalcium phosphate, powdered cork, or absorbent carbon black; water soluble polymers, resins, waxes; or solid fertilizers. Such solid compositions may, if desired, contain one or more compatible wetting, dispersing, emulsifying or colouring agents which, when solid, may also serve as a diluent.

The carrier may also'be liquid, for example: water; alcohols, particularly butanol or glycol, as well as their ethers or esters, particularly methylglycol acetate; ketones, particularly acetone, cyclohexanone, methylethyl ketone, methylisobutylketone, or isophorone; petroleum fractions such as paraffinic or aromatic hydrocarbons, particularly xylenes or alkyl naphthalenes; mineral or vegetable oils; aliphatic chlorinated hydrocarbons, particularly trichloroethane or methylene chloride; aromatic chlorinated hydrocarbons, particularly chlorobenzenes; water-soluble or strongly polar solvents such as dimethylformamide, dimethyl sulphoxide, or N-methylpyrrolidone; liquefied gases; or the like or a mixture thereof.

The surface-active agent may be an emulsifying agent, dispersing agent or wetting agent of the ionic or non-ionic type or a mixture of such surface-active agents. Amongst these are e.g., salts of polyacrylic acids, salts of lignosulphonic acids, salts of phenolsulphonic or naphthalenesulphonic acids, polycondensates of ethylene oxide with fatty alcohols or fatty acids or fatty esters or fatty amines, substituted phenols (particularly alkylphenols or arylphenols), salts of sulphosuccinic acid esters, taurine derivatives (particularly alkyltaurates), phosphoric esters of alcohols or of polycondensates of ethylene oxide with phenols, esters of fatty acids with polyols, or sulphate, sulphonate or phosphate functional derivatives of the above compounds. The presence of at least one surface-active agent is generally essential when the active ingredient and/or the inert carrier are only slightly water soluble or are not water soluble and the carrier agent of the composition for application is water. Compositions of the invention may further contain other additives such as adhesives or colorants. Adhesives such as carboxymethylcellulose or natural or synthetic polymers in the form of powders, granules or lattices, such as arabic gum, polyvinyl alcohol or polyvinyl acetate, natural phospholipids, such as cephalins or lecithins, or synthetic phospholipids can be used in the formulations. It is possible to use colorants such as inorganic pigments, for example: iron oxides, titanium oxides or Prussian Blue; organic dyestuffs, such as alizarin dyestuffs, azo dyestuffs or metal phthalocyanine dyestuffs; or trace nutrients such as salts of iron, manganese, boron, copper, cobalt, molybdenum or zinc.

For their agricultural application, the compounds of the invention are therefore generally in the form of compositions, which are in various solid or liquid forms. Solid forms of compositions which can be used are dusting powders (with a content of the compound of the invention, ranging up to 80%), wettable powders or granules (including water dispersible granules), particularly those obtained by extrusion, compacting, impregnation of a granular carrier, or granulation starting from a powder (the content of the compound of the invention, in these wettable powders or granules being between about 0.5 and about 80%). Solid homogenous or heterogenous compositions containing one or more compounds of the invention, for example granules, pellets, briquettes or capsules, may be used to treat standing or running water over a period of time. A similar effect may be achieved using trickle or intermittent feeds of water dispersible concentrates as described herein. Liquid compositions, for example, include aqueous or non-aqueous solutions or suspensions (such as emulsifiable concentrates, emulsions, flowables, dispersions, or solutions) or aerosols. Liquid compositions also include, in particular, emulsifiable concentrates, dispersions, emulsions, flowables, aerosols, wettable powders (or powder for spraying), dry flowables or pastes as forms of compositions which are liquid or intended to form liquid compositions when applied, for example as aqueous sprays (including low and ultra-low volume) or as fogs or aerosols.

Liquid compositions, for example, in the form of emulsifiable or soluble concentrates most frequently comprise about 5 to about 80% by weight of the active ingredient, while the emulsions or solutions which are ready for application contain, in their case, about 0.01 to about 20% of the active ingredient. Besides the solvent, the emulsifiable or soluble concentrates may contain, when required, about 2 to about 50% of suitable additives, such as stabilizers, surface-active agents, penetrating agents, corrosion inhibitors, colorants or adhesives. Emulsions of any required concentration, which are particularly suitable for application, for example, to plants, may be obtained from these concentrates by dilution with water. These compositions are included within the scope of the compositions which may be employed in the present invention. The emulsions may be in the form of water-in-oil or oil-in-water type and they may have a thick consistency.

The liquid compositions of this invention may, in addition to normal agricultural use applications be used for example to treat substrates or sites infested or liable to infestation by arthropods (or other pests controlled by compounds of this invention) including premises, outdoor or indoor storage or processing areas, containers or equipment or standing or running water.

All these aqueous dispersions or emulsions or spraying mixtures can be applied, for example, to crops by any suitable means, chiefly by spraying, at rates which are generally of the order of about 100 to about 1,200 liters of spraying mixture per hectare, but may be higher or lower (eg. low or ultra-low volume) depending upon the need or application technique. The compound or compositions according to the invention are conveniently applied to vegetation and in particular to roots or leaves having pests to be eliminated. Another method of application of the compounds or compositions according to the invention is by chemigation, that is to say, the addition of a formulation containing the active ingredient to irrigation water. This irrigation may be sprinkler irrigation for foliar pesticides or it can be ground irrigation or underground irrigation for soil or for systemic pesticides.

The concentrated suspensions, which can be applied by spraying, are prepared so as to produce a stable fluid product which does not settle (fine grinding) and usually contain from about 10 to about 75% by weight of active ingredient, from about 0.5 to about 30% of surface-active agents, from about 0.1 to about 10% of thixotropic agents, from about 0 to about 30% of suitable additives, such as anti-foaming agents, corrosion inhibitors, stabilizers, penetrating agents, adhesives and, as the carrier, water or an organic liquid in which the active ingredient is poorly soluble or insoluble Some organic solids or inorganic salts may be dissolved in the carrier to help prevent settling or as antifreezes for water.

The wettable powers (or powder for spraying) are usually prepared so that they contain from about 10 to about 80% by weight of active ingredient, from about 20 to about 90% of a solid carrier, from about 0 to about 5% of a wetting agent, from about 3 to about 10% of a dispersing agent and, when necessary, from about 0 to about 80% of one or more stabilizers and/or other additives, such as penetrating agents, adhesives, anti-caking agents, colorants, or the like. To obtain these wettable powders, the active ingredient is thoroughly mixed in a suitable blender with additional substances which may be impregnated on the porous filler and is ground using a mill or other suitable grinder. This produces wettable powders, the wettability and the suspendability of which are advantageous. They may be suspended in water to give any desired concentration and this suspension can be employed very advantageously in particular for application to plant foliage.

The "water dispersible granules (WG)" (granules which are readily dispersible in water) have compositions which are substantially close to that of the wettable powders. They may be prepared by granulation of formulations described for the wettable powders, either by a wet route (contacting finely divided active ingredient with the inert filler and a little water, e.g. 1 to 20% by weight, or with an aqueous solution of a dispersing agent or binder, followed by drying and screening), or by a dry route (compacting followed by grinding and screening).

The rates and concentrations of the formulated compositions may vary according to the method of application or the nature of the compositions or use thereof. Generally speaking, the compositions for application to control arthropod or plant nematode pests usually contain from about 0.00001% to about 95%, more particularly from about 0.0005% to about 50% by weight of one or more compounds of the invention, or of total active ingredients (that is to say the compounds of the invention, together with other substances toxic to arthropods or plant nematodes, synergists, trace elements or stabilizers). The actual compositions employed and their rate of application will be selected to achieve the desired effect(s) by the farmer, livestock producer, medical or veterinary practitioner, pest control operator or other person skilled in the art.

Solid or liquid compositions for application topically to animals, timber, stored products or household goods usually contain from about 0.00005% to about 90%, more particularly from about 0.001% to about 10%, by weight of one or more compounds of the invention. For administration to animals orally or parenterally, including percutaneously solid or liquid compositions, these normally contain from about 0.1% to about 90% by weight of one or more compounds of the invention. Medicated feedstuffs normally contain from about 0.001% to about 3% by weight of one or more compounds of the invention. Concentrates or supplements for mixing with feedstuffs normally contain from about 5% to about 90%, preferably from about 5% to about 50%, by weight of one or more compounds of the invention. Mineral salt licks normally contain from about 0.1% to about 10% by weight of one or more compounds of formula (I) or pesticidally acceptable salts thereof.

Dusts or liquid compositions for application to livestock, goods, premises or outdoor areas may contain from about 0.0001% to about 15%, more especially from about 0.005% to about 2.0%, by weight, of one or more compounds of the invention. Suitable concentrations in treated waters are between about 0.0001 ppm and about 20 ppm, more particularly about 0.001 ppm to about 5.0 ppm of one or more compounds of the invention, and may be used therapeutically in fish farming with appropriate exposure times. Edible baits may contain from about 0.01% to about 5%, preferably from about 0.01% to about 1.0%, by weight, of one or more compounds of the invention.

When administered to vertebrates parenterally, orally or by percutaneous or other means, the dosage of compounds of the invention, will depend upon the species, age, or health of the vertebrate and upon the nature and degree of its actual or potential infestation by arthropod or helminth pests. A single dose of about 0.1 to about 100 mg, preferably about 2.0 to about 20.0 mg, per kg body weight of the animal or doses of about 0.01 to about 20.0 mg, preferably about 0.1 to about 5.0 mg, per kg body weight of the animal per day, for sustained medication, are generally suitable by oral or parenteral administration. By use of sustained release formulations or devices, the daily doses required over a period of months may be combined and administered to animals on a single occasion.

The following composition EXAMPLES 2A-2M illustrate compositions for use against arthropods, especially mites or insects, or plant nematodes, which comprise, as active ingredient, compounds of the invention, such as those described in preparative examples. The compositions described in EXAMPLES 2A-2M can each be diluted to give a sprayable composition at concentrations suitable for use in the field. Generic chemical descriptions of the ingredients (for which all of the following percentages are in weight percent), used in the composition EXAMPLES 2A-2M exemplified below, are as follows:

| Trade Name | Chemical Description |
| --- | --- |
| Ethylan BCP | Nonylphenol ethylene oxide condensate |
| Soprophor BSU | Tristyrylphenol ethylene oxide condensate |
| Arylan CA | A 70% w/v solution of calcium dodecylbenzenesulfonate |
| Solvesso 150 | Light $C_{10}$ aromatic solvent |
| Arylan S | Sodium dodecylbenzenesulfonate |
| Darvan $NO_2$ | Sodium lignosulphonate |
| Celite PF | Synthetic magnesium silicate carrier |
| Sopropon T36 | Sodium salts of polycarboxylic acids |
| Rhodigel 23 | Polysaccharide xanthan gum |
| Bentone 38 | Organic derivative of magnesium montmorillonite |
| Aerosil | Microfine silicon dioxide |

Example 2A

A water soluble concentrate is prepared with the composition as follows:

| | |
| --- | --- |
| Active ingredient | 7% |
| Ethylan BCP | 10% |
| N-methylpyrrolidone | 83% |

To a solution of Ethylan BCP dissolved in a portion of N-methylpyrrolidone is added the active ingredient with heating and stirring until dissolved. The resulting solution is made up to volume with the remainder of the solvent.

Example 2B

An emulsifiable concentrate (EC) is prepared with the composition as follows:

| | |
| --- | --- |
| Active ingredient | 25%(max) |
| Soprophor BSU | 10% |
| Arylan CA | 5% |
| N-methylpyrrolidone | 50% |
| Solvesso 150 | 10% |

The first three components are dissolved in N-methylpyrrolidone and to this is then added the Solvesso 150 to give the final volume.

Example 2C

A wettable powder (WP) is prepared with the composition as follows:

|  |  |
|---|---|
| Active ingredient | 40% |
| Arylan S | 2% |
| Darvan NO$_2$ | 5% |
| Celite PF | 53% |

The ingredients are mixed and ground in a hammer-mill to a powder with a particle size of less than 50 microns.

Example 2D

An aqueous-flowable formulation is prepared with the composition as follows:

|  |  |
|---|---|
| Active ingredient | 40.00% |
| Ethylan BCP | 1.00% |
| Sopropon T360. | 0.20% |
| Ethylene glycol | 5.00% |
| Rhodigel 230. | 0.15% |
| Water | 53.65% |

The ingredients are intimately mixed and are ground in a bead mill until a mean particle size of less than 3 microns is obtained.

Example 2E

An emulsifiable suspension concentrate is prepared with the composition as follows:

|  |  |
|---|---|
| Active ingredient | 30.0% |
| Ethylan BCP | 10.0% |
| Bentone 38 | 0.5% |
| Solvesso 150 | 59.5% |

The ingredients are intimately mixed and ground in a bead-mill until a mean particle size of less than 3 microns is obtained.

Example 2F

A water dispersible granule is prepared with the composition as follows:

|  |  |
|---|---|
| Active ingredient | 30% |
| Darvan No 2 | 15% |
| Arylan S | 8% |
| Celite PF | 47% |

The ingredients are mixed, micronized in a fluid-energy mill and then granulated in a rotating pelletizer by spraying with water (up to 10%). The resulting granules are dried in a fluid-bed drier to remove excess water.

Example 2G

A dusting powder is prepared with the composition as follows:

|  |  |
|---|---|
| Active ingredient | 1 to 10% |
| Talc powder-superfine | 99 to 90% |

The ingredients are intimately mixed and further ground as necessary to achieve a fine powder. This powder may be applied to a locus of arthropod infestation, for example refuse dumps, stored products or household goods or animals infested by, or at risk of infestation by, arthropods to control the arthropods by oral ingestion. Suitable means for distributing the dusting powder to the locus of arthropod infestation include mechanical blowers, handshakers or livestock self treatment devices.

Example 2H

An edible bait is prepared with the composition as follows:

|  |  |
|---|---|
| Active ingredient | 0.1 to 1.0% |
| Wheat flour | 80% |
| Molasses | 19.9 to 19% |

The ingredients are intimately mixed and formed as required into a bait form. This edible bait may be distributed at a locus, for example domestic or industrial premises, e.g. kitchens, hospitals or stores, or outdoor areas, infested by arthropods, for example ants, locusts, cockroaches or flies, to control the arthropods by oral ingestion.

Example 2I

A solution formulation is prepared with a composition as follows:

|  |  |
|---|---|
| Active ingredient | 15% |
| Dimethyl sulfoxide | 85% |

The active ingredient is dissolved in dimethyl sulfoxide with mixing and or heating as required. This solution may be applied percutaneously as a pour-on application to domestic animals infested by arthropods or, after sterilization by filtration through a polytetrafluoroethylene membrane (0.22 micrometer pore size), by parenteral injection, at a rate of application of from 1.2 to 12 ml of solution per 100 kg of animal body weight.

Example 2J

A wettable powder is prepared with the composition as follows:

|  |  |
|---|---|
| Active ingredient | 50% |
| Ethylan BCP | 5% |
| Aerosil | 5% |
| Celite PF | 40% |

The Ethylan BCP is absorbed onto the Aerosil which is then mixed with the other ingredients and ground in a hammer-mill to give a wettable powder, which may be diluted with water to a concentration of from 0.001% to 2% by weight of the active compound and applied to a locus of infestation by arthropods, for example, dipterous larvae or plant nematodes, by spraying, or to domestic animals infested by, or at risk of infection by arthropods, by spraying or dipping, or by oral administration in drinking water, to control the arthropods.

Example 2K

A slow release bolus composition is formed from granules containing the following components in varying percentages (similar to those described for the previous compositions) depending upon need:
Active ingredient
Density agent
Slow-release agent
Binder The intimately mixed ingredients are formed into granules which are compressed into a bolus with a specific gravity of 2 or more. This can be administered orally to ruminant domestic animals for retention within the reticulo-rumen to give a continual slow release of active compound over an extended period of time to control infestation of the ruminant domestic animals by arthropods.

Example 2L

A slow release composition in the form of granules, pellets, brickettes or the like can be prepared with compositions as follows:
Active ingredient 0.5 to 25%
Polyvinyl chloride 75 to 99.5%
Dioctyl phthalate (plasticizer)

The components are blended and then formed into suitable shapes by melt-extrusion or molding. These composition are useful, for example, for addition to standing water or for fabrication into collars or eartags for attachment to domestic animals to control pests by slow release.

Example 2M

A water dispersible granule is prepared with the composition as follows:

| | |
|---|---|
| Active ingredient | 85% (max) |
| Polyvinylpyrrolidone | 5% |
| Attapulgite clay | 6% |
| Sodium lauryl sulfate | 2% |
| Glycerine | 2% |

The ingredients are mixed as a 45% slurry with water and wet milled to a particle size of 4 microns, then spray-dried to remove water.

Methods of Pesticidal Use

The following representative test procedures, using compounds of the invention, were conducted to determine the parasiticidal and pesticidal activity of compounds of the invention.

METHOD A: Screening method to test systemicity of compounds against *Ctenocephalides felis* (Cat flea)

A test container was filled with 10 adults of *Ctenocephalides felis*. A glass cylinder was closed on one end with parafilm and placed on top of the test container. The test compound solution was then pipetted into bovine blood and added to the glass cylinder. The treated *Ctenocephalides felis* were held in this artificial dog test (blood 37° C., 40-60% relative humidity; *Ctenocephalides felis* 20-22° C., 40-60% relative humidity) and assessment performed at 24 and 48 hours after application. Active compounds gave at least 90% control of *Ctenocephalides felis* at a test concentration of 5 ppm or less.

METHOD B: *Diabrotica undecimpunctata* (southern corn rootworm) screen

Two days before application, seeds of maize were soaked in water under warm conditions to elicit fast germination. One day before application, eggs of *Diabrotica undecimpunctata* were transferred to one half of a Japanese filter paper placed in a plastic petri dish. Afterwards, a sprouted maize seed was placed on a moistened pad beside the filter paper. Three drops of 200 microliters of test compound solution were carefully pipetted onto the egg. The remainder of the solution was placed on the maize and then the Petri dish was closed. The treated eggs in the Petri dishes were held in a climate chamber for 6 days. The compound efficacy (percentage of dead eggs and/or larvae in comparison to untreated control) was assessed 6 days after application using a binocular microscope.

Active compounds gave at least 90% control of *Diabrotica undecimpunctata* at a test concentration of 10 ppm.

METHOD C: *Nephotettix* Cinciceps (rice leafhopper) screen

The leaves of 12 rice plants having a stem length of 8 cm were dipped for 5 seconds into an aqueous solution of the formulated test compound. After the solution had run off, the rice plants treated in this manner were placed in a Petri dish and populated with about 20 larvae (L3 stage) of *Nephotettix cincticeps*. The Petri dish was closed and then stored in a climate chamber (16 hours of light/day, 25° C., 40-60% relative humidity). After 6 days storage, the percentage mortality of leafhopper larvae was determined.

Active compounds gave at least 98% mortality of *Nephotettix cinciceps* larvae at a test concentration of 100 ppm.

METHOD D: Screening method to test contact activity against *Ctenocephalides felis* (Cat flea)

Solutions of the test compounds were dropped onto filter paper, dried and the filter paper placed into test tubes and infested with 10 adults of *Ctenocephalides felis*. The treated *Ctenocephalides felis* were held in a climate chamber (26° C., 80% RH) and the percentage efficacy assessed 24 hours and 48 hours after application in comparison with the untreated control.

Active compounds gave at least 70% contact control of *Ctenocephalides felis* at a test concentration of 1000 ppm.

METHOD E: Screening method to test contact activity against *Rhipicephalus sanguineus* (Brown dog tick)

Solutions of the test compounds were dropped onto filter paper, dried and the filter paper placed into test tubes and infested with 20-30 larvae (L1) of *Rhipicephalus sanguineus* and the tubes closed with a clip. The treated *Rhipicephalus sanguineus* were held in a climate chamber (25° C., 90% RH) and the percentage efficacy assessed 24 hours after application in comparison with the untreated control. Active compounds gave at least 70% contact control of *Rhipicephalus sanguineus* at a test concentration of 100 ppm.

The following Compound numbers were active in one or more of the above tests: 1-1, 1-2, 1-16, 1-44, 1-72, 1-85, 1-87, 1-90, 1-93, 1-94, 1-95, 1-96, 1-97, 1-116, 1-114, 1-115, 1-117, 1-118, 1-119, 1-120, 1-121, 1-122, 1-123, 1-124, 1-125, 1-126, 2-2, 2-16, 2-30, 2-45, 248, 2-51, 2-57, 2-58, 2-74, 2-80, 2-86, 2-92, 2-94, 2-109, 2-115, 2-121, 2-127, 2-128, 2-129, 2-144, 2-148, 2-149, 2-150, 2-151, 4-32, 4-33, 4-34, 4-35, 5-1, 5-9, 5-15, 5-16, 5-22, 5-30, 5-32, 5-36, 5-38, 540, 542, 5-46, 547, 5-48, 5-54, 560, 5-61, 5-75, 5-77, 5-81, 5-83, 5-86, 5-87, 5-88, 5-89, 5-150, 5-151 and 7-32.

The invention claimed is:

1. A compound of formula (I):

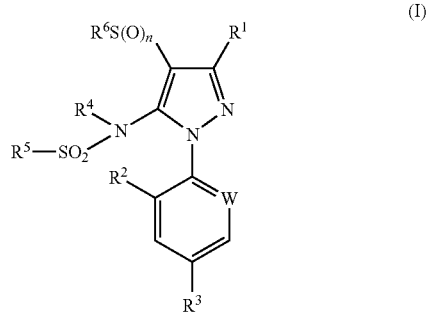

wherein:
- $R^1$ is $(C_1-C_6)$-alkyl, $(C_1-C_6)$-haloalkyl, CN, $C(S)NH_2$, or halogen;
- W is, $C-CH_3$ or C-halogen;
- $R^2$ is H, $CH_3$ or halogen;
- $R^3$ is halo, $(C_1-C_6)$-alkyl, $(C_1-C_6)$-haloalkyl, $(C_1-C_6)$-haloalkoxy, $S(O)_p-(C_1-C_6)$-haloalkyl or $SF_5$;
- $R^4$ is $(C_2-C_6)$-alkenyl, $(C_2-C_6)$-haloalkenyl, $(C_2-C_6)$-alkynyl, $(C_2-C_6)$-haloalkynyl, $(C_3-C_7)$-cycloalkyl, $-CO_2-(C_1-C_6)$-alkyl, $-CO_2-(C_3-C_7)$-cycloalkyl, $-CO_2-(C_1-C_4)$-alkyl-$(C_3-C_7)$-cycloalkyl, $-CO_2-(C_3-C_6)$-alkenyl, $-CO_2-(C_3-C_6)$-alkynyl, $-CO_2-(CH_2)_qR^7$, $CONR^8R^9$, $-CO_2-(CH_2)_qR^1$, $-(CH_2)_qR^7$, $(CH_2)_qR^1$, $COR^9$, $COCH_2NR^8R^9$, $-CO-(CH_2)_qR^7$ or $(C_1-C_6)$-alkyl unsubstituted or substituted by one or more radicals selected from the group consisting of halogen, $(C_1-C_6)$-alkoxy, $(C_1-C_6)$-haloalkoxy, $(C_3-C_7)$-cycloalkyl, $S(O)_pR^{11}$, $CO_2-(C_1-C_6)$-alkyl, $-O(C=O)-(C_1-C_6)$-alkyl, $NR^8R^9$, $CONR^8R^9$, $SO_2NR^8R^9$, OH, CN, $NO_2$, $OR^7$, $NR^8COR^{12}$ and $NR^8SO_2R^{11}$;
- $R^5$ is $(C_3-C_7)$-cycloalkyl, $(C_2-C_6)$-alkenyl, $(C_2-C_6)$-haloalkenyl, $R^{13}$ or $-CH=CH-R^{15}$; or is $(C_1-C_{15})$-alkyl unsubstituted or substituted by one or more radicals selected from the group consisting of halogen, $(C_1-C_6)$-alkoxy, $(C_1-C_6)$-haloalkoxy, $(C_3-C_6)$-alkenyloxy, $(C_3-C_6)$-haloalkenyloxy, $(C_3-C_6)$-alkynyloxy, $(C_3-C_6)$-haloalkynyloxy, $(C_3-C_7)$-cycloalkyl, $S(O)_pR^7$, $S(O)_pR^{11}$, CN, $NO_2$, OH, $COR^8$, $NR^8COR^{12}$, $NR^8SO_2R^{11}$, $CONR^8R^9$, $NR^8R^9$, $OR^7$, $R^{13}$ and $CO_2R^8$, or a methylene group in the unsubstituted or substituted $(C_1-C_6)$-alkyl is replaced by a group selected from $-CO-$, $-O-$, $-S(O)_p-$, $-NR^8-$, $-COO-$, $-OCO-$, $-CONR^8-$, $-NR^8CO-$, $-C(=NOR^8)-$, $-C(=N-NR^8R^9)-$ and $-C(=NR^8)-$ provided that the replacing group is not directly bonded to the $SO_2$ group in formula (I);
- $R^6$ and $R^{11}$ are each independently $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl or $(C_3-C_7)$-cycloalkyl;
- $R^7$ is phenyl unsubstituted or substituted by one or more radicals selected from the group consisting of halogen, $(C_1-C_6)$-alkyl, $(C_1-C_6)$-haloalkyl, $(C_1-C_6)$-alkoxy, $(C_1-C_6)$-haloalkoxy, CN, $NO_2$, $S(O)_pR^{11}$ and $NR^9R^{12}$;
- $R^8$ is H, $(C_1-C_6)$-alkyl, $(C_1-C_6)$-haloalkyl, $(C_3-C_7)$-cycloalkyl, $-(C_1-C_4)$-alkyl-$(C_3-C_7)$-cycloalkyl, or $-(CH_2)_qR^7$;
- $R^9$ and $R^{12}$ are each independently H, $(C_1-C_6)$-alkyl, $(C_1-C_6)$-haloalkyl, $(C_3-C_7)$-cycloalkyl or $-(C_1-C_4)$-alkyl-$(C_3-C_7)$-cycloalkyl;
- $R^{13}$ is aryl unsubstituted or substituted by one or more radicals selected from the group consisting of halogen, $(C_1-C_6)$-alkyl, $(C_1-C_6)$-haloalkyl, $(C_1-C_6)$-alkoxy, $(C_1-C_6)$-haloalkoxy, CN, $NO_2$, $S(O)_pR^{11}$, $SF_5$, $NR^8R^9$, $COR^{11}$, $COR^7$, $CONR^8R^9$, $SO_2NR^8R^9$, OH, $OR^7$, $R^{15}$, $SO_3H$, $(C_1-C_6)$-alkylideneimino, $CH=NOR^{14}$, $S(O)_pR^{18}$, and $CO_2R^{19}$;
- $R^{14}$ is $(C_1-C_6)$-alkyl or $(C_1-C_6)$-haloalkyl;
- $R^{15}$ is phenyl or naphthyl which groups are unsubstituted or substituted by one or more radicals selected from the group consisting of halogen, $(C_1-C_6)$-alkyl, $(C_1-C_6)$-haloalkyl and $(C_1-C_6)$-alkoxy;
- $R^{18}$ is phenyl unsubstituted or substituted by one or more radicals selected from the group consisting of halogen, $(C_1-C_6)$-alkyl, $(C_1-C_6)$-haloalkyl and $(C_1-C_6)$-alkoxy;
- $R^{19}$ is $(C_1-C_6)$-alkyl, $(C_1-C_6)$-haloalkyl, $R^{13}$ or $-(C_1-C_6)$-alkyl-$(C_1-C_3)$-alkoxy;
- n, p and q are each independently zero, one or two;

or a pesticidally acceptable salt thereof.

2. A compound or a salt thereof as claimed in claim 1 wherein:
- $R^1$ is $(C_1-C_6)$-alkyl, $(C_1-C_6)$-haloalkyl, CN, $C(S)NH_2$, or halogen;
- W is, $C-CH_3$ or C-halogen;
- $R^2$ is H, $CH_3$ or halogen;
- $R^3$ is halo, $(C_1-C_6)$-alkyl, $(C_1-C_6)$-haloalkyl, $(C_1-C_6)$-haloalkoxy, $S(O)_p-(C_1-C_6)$-haloalkyl or $SF_5$;
- $R^4$ is $(C_2-C_6)$-alkenyl, $(C_2-C_6)$-haloalkenyl, $(C_2-C_6)$-alkynyl, $(C_2-C_6)$-haloalkynyl, $(C_3-C_7)$-cycloalkyl, $-CO_2-(C_1-C_6)$-alkyl, $-CO_2-(C_3-C_7)$-cycloalkyl, $-CO_2-(C_1-C_4)$-alkyl-$(C_3-C_7)$-cycloalkyl, $-CO_2-(C_3-C_6)$-alkenyl, $-CO_2-(C_3-C_6)$-alkynyl, $-CO_2-(CH_2)_qR^7$, $CONR^8R^9$, $CO_2-(CH_2)_qR^{10}$, $-(CH_2)_qR^7$, $-(CH_2)_qR^{10}$, $COR^9$, $COCH_2NR^8R^9$, $-CO-(CH_2)_qR^7$; or $(C_1-C_6)$-alkyl unsubstituted or substituted by one or more radicals selected from the group consisting of halogen, $(C_1-C_6)$-alkoxy, $(C_1-C_6)$-haloalkoxy, $(C_3-C_7)$-cycloalkyl, $S(O)_pR^{11}$, $CO_2-(C_1-C_6)$-alkyl, $-O(C=O)-(C_1-C_6)$-alkyl, $NR^8R^9$, $CONR^8R^9$, $SO_2NR^8R^9$, OH, CN, $NO_2$, $OR^7$, $NR^8COR^{12}$ and $NR^8SO_2R^{11}$;
- $R^5$ is $(C_3-C_7)$-cycloalkyl, $(C_2-C_6)$-alkenyl, $(C_2-C_6)$-haloalkenyl, $R^{13}$ or $-CH=CH-R^{15}$; or is $(C_1-C_6)$-alkyl unsubstituted or substituted by one or more radicals selected from the group consisting of halogen, $(C_1-C_6)$-alkoxy, $(C_1-C_6)$-haloalkoxy, $(C_3-C_6)$-alkenyloxy, $(C_3-C_6)$-haloalkenyloxy, $(C_3-C_6)$-alkynyloxy, $(C_3-C_6)$-haloalkynyloxy, $(C_3-C_7)$-cycloalkyl, $S(O)_pR^7$, $S(O)_pR^{11}$, CN, $NO_2$, OH, $COR^8$, $NR^8COR^{12}$, $NR^8SO_2R^{11}$, $CONR^8R^9$, $NR^8R^9$, $OR^7$, $R^{13}$ and $CO_2R^8$, or a methylene group in the unsubstituted or substituted $(C_1-C_6)$-alkyl is replaced by a group selected from $-CO-$, $-O-$, $-S(O)_p-$, $-NR^8-$, $-COO-$, $-OCO-$, $-CONR^8-$, $-NR^8CO-$, $-C(=NOR^8)-$, $-C(=N-NR^8R^9)-$ and $-C(=NR^8)-$ provided that the replacing group is not directly bonded to the $SO_2$ group in formula (I);
- $R^6$ and $R^{11}$ are each independently $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl or $(C_3-C_7)$-cycloalkyl;

R⁷ is phenyl unsubstituted or substituted by one or more radicals selected from the group consisting of halogen, $(C_1-C_6)$-alkyl, $(C_1-C_6)$-haloalkyl, $(C_1-C_6)$-alkoxy, $(C_1-C_6)$-haloalkoxy, CN, NO₂, S(O)$_p$R¹¹ and NR⁹R¹²;

R⁸ is H, $(C_1-C_6)$-alkyl, $(C_1-C_6)$-haloalkyl, $(C_3-C_7)$-cycloalkyl, —$(C_1-C_4)$-alkyl-$(C_3-C_7)$-cycloalkyl, or —(CH₂)$_q$R⁷;

R⁹ and R¹² are each independently H, $(C_1-C_6)$-alkyl, $(C_1-C_6)$-haloalkyl, $(C_3-C_7)$-cycloalkyl or —$(C_1-C_4)$-alkyl-$(C_3-C_7)$-cycloalkyl;

R¹³ is aryl unsubstituted or substituted by one or more radicals selected from the group consisting of halogen, $(C_1-C_6)$-alkyl, $(C_1-C_6)$-haloalkyl, $(C_1-C_6)$-alkoxy, $(C_1-C_6)$-haloalkoxy, CN, NO₂, S(O)$_p$R¹¹, SF₅, NR⁸R⁹, COR¹¹, COR⁷, CONR⁸R⁹, SO₂NR⁸R⁹, OH, OR⁷, R¹⁵, SO₃H and $(C_1-C_6)$-alkylideneimino;

R¹⁴ is $(C_1-C_6)$-alkyl or $(C_1-C_6)$-haloalkyl;

R¹⁵ is phenyl or naphthyl which groups are unsubstituted or substituted by one or more radicals selected from the group consisting of halogen, $(C_1-C_6)$-alkyl, $(C_1-C_6)$-haloalkyl and $(C_1-C_6)$-alkoxy.

3. A compound or a salt thereof as claimed in claim 1 wherein R¹ is CN.

4. A compound or a salt thereof as claimed in claim 1, wherein W is C—Cl.

5. A compound or a salt thereof as claimed in claim 1 wherein R² is chlorine.

6. A compound or a salt thereof as claimed in claim 1 wherein R³ is CF₃.

7. A compound or a salt thereof as claimed in claim 1 wherein R⁴ is $(C_3-C_6)$-alkenyl, $(C_3-C_6)$-alkynyl, $(C_3-C_7)$-cycloalkyl, —CO₂—$(C_1-C_6)$-alkyl, —(CH₂)$_q$R⁷ or COCH₂NR⁸R⁹; or $(C_1-C_6)$-alkyl unsubstituted or substituted by one or more radicals selected from the group consisting of halogen, $(C_3-C_7)$-cycloalkyl and S(O)$_p$R¹¹.

8. A compound or a salt thereof as claimed in claim 1 wherein R⁵ is R¹³; or $(C_1-C_6)$-alkyl unsubstituted or substituted by one or more radicals selected from the group consisting of halogen and R¹³.

9. A compound or a salt thereof as claimed in claim 1 wherein R⁶ is CF₃.

10. A compound or a salt thereof as claimed in claim 1 wherein

R¹ is CN;
W is C—Cl;
R² is chlorine;
R³ is CF₃;
R⁴ is $(C_3-C_4)$-alkenyl, $(C_3-C_4)$-alkynyl, $(C_3-C_6)$-cycloalkyl, —CO₂—$(C_1-C_3)$-alkyl, —(CH₂)$_q$R⁷ or COCH₂NR⁸R⁹; or $(C_1-C_4)$-alkyl unsubstituted or substituted by one or more radicals selected from the group consisting of halogen, $(C_3-C_6)$-cycloalkyl and S(O)$_p$R¹¹;
R⁵ is R¹³; or $(C_1-C_4)$-alkyl unsubstituted or substituted by one or more radicals selected from the group consisting of halogen, R¹³;
R⁶ is CF₃;
R⁷ is phenyl unsubstituted or substituted by one or more radicals selected from the group consisting of halogen, $(C_1-C_2)$-alkyl, $(C_1-C_2)$-haloalkyl and $(C_1-C_2)$-alkoxy;
R⁸ is H or $(C_1-C_3)$-alkyl;
R⁹ is H or $(C_1-C_3)$-alkyl;
R¹¹ and R¹⁴ are each independently $(C_1-C_2)$-alkyl or $(C_1-C_2)$-haloalkyl;
R¹³ is phenyl unsubstituted or substituted by one or more radicals selected from the group consisting of halogen,
$(C_1-C_2)$-alkyl, $(C_1-C_2)$-haloalkyl, $(C_1-C_2)$-alkoxy, $(C_1-C_2)$-haloalkoxy, CN, NO₂, S(O)$_p$R¹¹ and NR⁸R⁹;

n and p are each independently 0, 1 or 2;

q is 0 or 1.

11. A process for the preparation of a compound of formula (I) or a salt thereof as defined in claim 1, which process comprises:
  a) where R¹, R², R³, R⁴, R⁵, R⁶, W and n are as defined in claim 1, reacting a compound of formula (II):

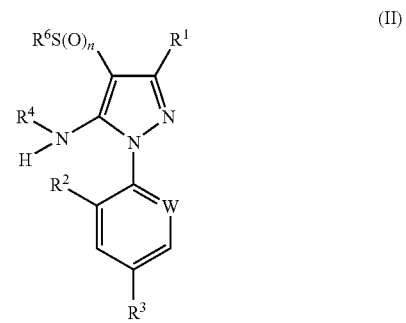

wherein R¹, R², R³, R⁴, R⁶, W and n are as defined in claim 1, with a compound of formula (III):

(A) R⁵—SO₂L¹     (III)

wherein R⁵ is as defined in claim 1 and L¹ is halogen; and b) if desired, converting a resulting compound of formula (I) into a pesticidally acceptable salt thereof.

12. A pesticidal composition for the control of arthropods and helminths comprising a pesticidally effective amount of a compound of formula (I) or a pesticidally acceptable salt thereof as defined in claim 1 for the control of arthropods and helminths, in association with a pesticidally acceptable diluent or carrier and/or surface active agent for the control of arthropods and helminths.

13. A method for the control of arthropods and helminths at a locus which comprises applying to said locus a pesticidally effective amount of a compound of formula (I) or a salt thereof according to claim 1.

14. A method for the control of arthropods and helminths at a locus which comprises applying to said locus a pesticidally effective amount of a composition as claimed in claim 12.

15. A method for the control of arthropods and helminths in or on an animal which comprises administering to said animal a pesticidally effective amount of a compound of formula (I) or a salt thereof as claimed in claim 1.

16. A method for the control of arthropods and helminths in or on an animal which comprises administering to said animal a pesticidally effective amount of a veterinary medicament as claimed in claim 12.

17. A compound as claimed in claim 1, which is selected from the group consisting of:

(a) the compound of formula

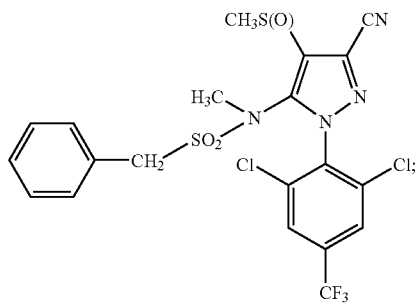

(b) the compound of the formula

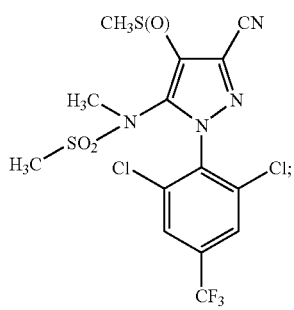

(c) the compound of the formula and (d) the pesticidally acceptable salts thereof.

18. The pesticidal composition of claim 12, wherein the arthropods and helminths are selected from the group consisting of insects, arachnids, nematodes and combinations thereof.

19. The method of claim 15, wherein the arthropods and helminths are selected from the group consisting of insects, arachnids, nematodes and combinations thereof.

* * * * *